US012367791B1

(12) United States Patent
Standley et al.

(10) Patent No.: US 12,367,791 B1
(45) Date of Patent: Jul. 22, 2025

(54) AUTOINJECTOR TRAINING DEVICE

(71) Applicant: Windgap Medical, Inc., Watertown, MA (US)

(72) Inventors: Adam Standley, Cambridge, MA (US); Cole Constantineau, Cambridge, MA (US); Aaron Kapelus, Cambridge, MA (US); Evan Sherr, Watertown, MA (US); Jeffrey Chagnon, Somerville, MA (US)

(73) Assignee: Windgap Medical, Inc., Watertown, MA (US)

( * ) Notice: Subject to any disclaimer, the term of this patent is extended or adjusted under 35 U.S.C. 154(b) by 1219 days.

(21) Appl. No.: 17/035,328

(22) Filed: Sep. 28, 2020

Related U.S. Application Data

(60) Provisional application No. 62/906,879, filed on Sep. 27, 2019.

(51) Int. Cl.
  *G09B 23/28* (2006.01)
  *A61M 5/20* (2006.01)
  *A61M 5/32* (2006.01)

(52) U.S. Cl.
  CPC ......... *G09B 23/285* (2013.01); *A61M 5/2033* (2013.01); *A61M 5/3202* (2013.01)

(58) Field of Classification Search
  CPC .. A61M 5/2033; A61M 5/3202; G09B 23/285
  USPC ........................................................ 434/262
  See application file for complete search history.

(56) References Cited

U.S. PATENT DOCUMENTS

| | | | | |
|---|---|---|---|---|
| 5,071,353 | A * | 12/1991 | van der Wal | A61M 5/2033 434/262 |
| 5,567,160 | A * | 10/1996 | Massino | G09B 23/285 434/262 |
| 7,682,155 | B2 | 3/2010 | Raven et al. | |
| 8,679,061 | B2 * | 3/2014 | Julian | A61P 43/00 604/157 |
| 9,132,236 | B2 * | 9/2015 | Karlsson | A61M 5/32 |
| 9,443,445 | B2 * | 9/2016 | Laurusonis | G09B 23/285 |
| 10,089,902 | B2 * | 10/2018 | Baker | G09B 19/24 |
| 10,127,836 | B2 * | 11/2018 | Alexandersson | G09B 23/285 |
| 10,235,905 | B2 * | 3/2019 | Su | G09B 23/285 |
| 10,350,364 | B2 * | 7/2019 | Standley | A61M 5/19 |
| 10,391,262 | B2 * | 8/2019 | Durvasula | A61M 5/31596 |
| 11,069,260 | B2 * | 7/2021 | Baker | G09B 23/285 |
| 11,087,640 | B2 * | 8/2021 | Daniel | A61M 5/3157 |
| 11,107,369 | B2 * | 8/2021 | Chang | G09B 23/285 |
| 11,276,327 | B2 * | 3/2022 | Boström | G09B 23/00 |
| 11,276,328 | B2 * | 3/2022 | Chang | G09B 23/285 |
| 11,551,580 | B2 * | 1/2023 | Baker | G09B 19/003 |
| 2007/0111175 | A1 * | 5/2007 | Raven | G09B 23/285 434/262 |
| 2014/0276568 | A1 * | 9/2014 | Worden | G09B 23/285 434/262 |

(Continued)

*Primary Examiner* — Joseph B Baldori
(74) *Attorney, Agent, or Firm* — Stephen J. Kenny; Foley Hoag LLP

(57) ABSTRACT

An injector training device configured to mimic a real portable autoinjector mixing and delivery device including mimicking pressure required to twist the cap, various clicking noises, bump trigger, and the extension of the bump trigger that mimics a lockout needle shield. The injector training device is also configured to be resettable for multiple training sessions.

18 Claims, 58 Drawing Sheets

(56) References Cited

U.S. PATENT DOCUMENTS

| | | | | |
|---|---|---|---|---|
| 2015/0100024 A1* | 4/2015 | Baker | ............... | A61M 5/20 |
| | | | | 434/262 |
| 2016/0049098 A1* | 2/2016 | Swanson | ............ | G09B 23/285 |
| | | | | 434/262 |
| 2017/0069230 A1* | 3/2017 | Baker | ............ | G09B 23/285 |
| 2017/0148354 A1* | 5/2017 | Baker | ............ | A61M 5/326 |
| 2017/0352293 A1* | 12/2017 | Baker | ............ | G09B 23/285 |
| 2020/0139048 A1* | 5/2020 | Buchine | ............ | A61M 5/44 |
| 2020/0258425 A1* | 8/2020 | Foley | ............ | A61M 5/3202 |
| 2021/0268198 A1* | 9/2021 | Baker | ............ | A61M 5/31543 |
| 2022/0215779 A1* | 7/2022 | Yin | ............ | A61M 5/31501 |

* cited by examiner

Cont. from Fig. 11C

UI7: User depresses TA axially to its stowed position 4.2 Spring compresses 4.3 Anti-rotation snap tab aligns with TA snap recess 4.4 TA two-way snaps engage with Drum, make 'clicking' sound, and retain TA UI8: User replaces cap by aligning and pushing cap onto frame 4.5 Cap gear (spline) aligns Drum reset snaps 4.6 Cap contacts Frame flange at end of travel UI9: User rotates cap CW to stowed position Cont. to Fig. 11E

FIG. 11D

Cont. from Fig. 11D 4.8 Cap spline passes by Drum reset snap, makes 'clicking' sound 4.9 Cap over-rides Frame Protrusion, makes 'clicking' sound 4.10 Cap reaches end of travel contacting Frame Protrusion

FIG. 11E

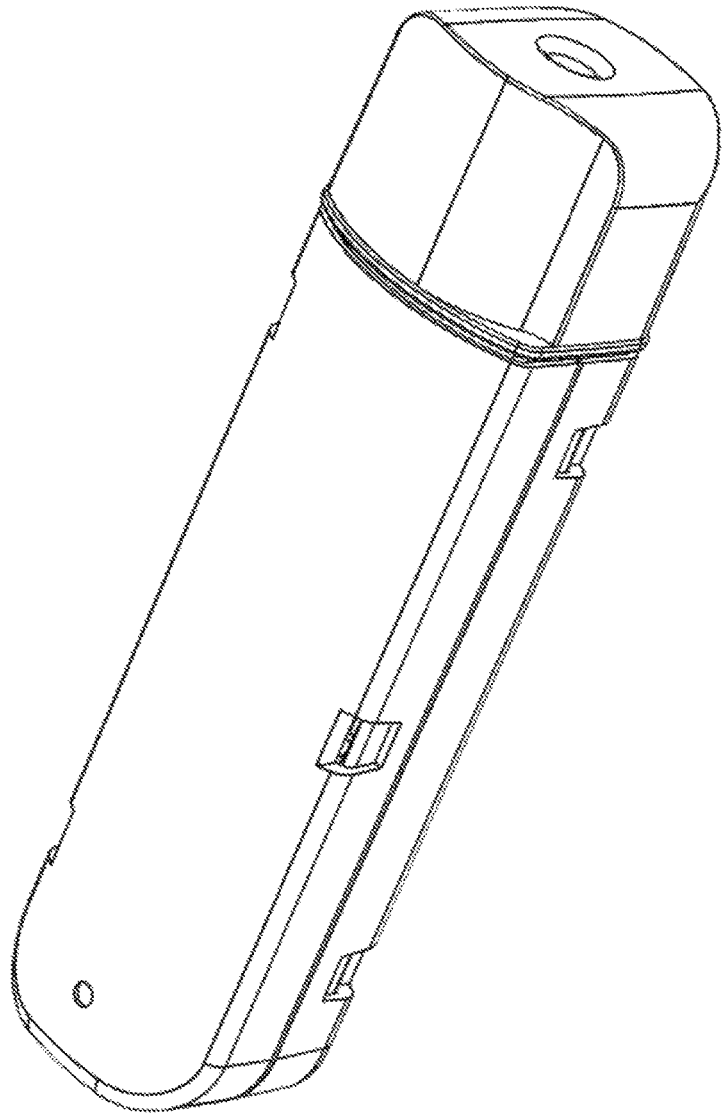
FIG. 12A — S0. Stowed State

UI1: User Twists Cap Counterclockwise (CCW)

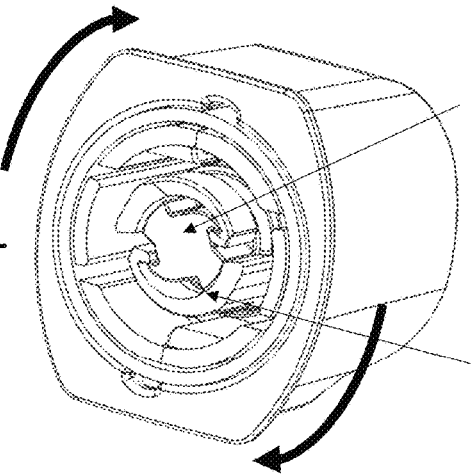
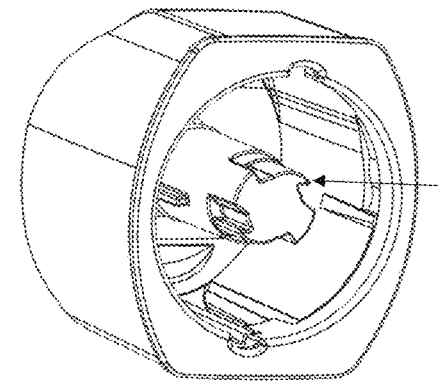
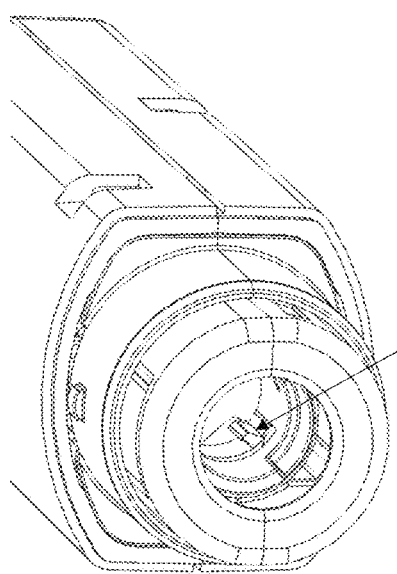
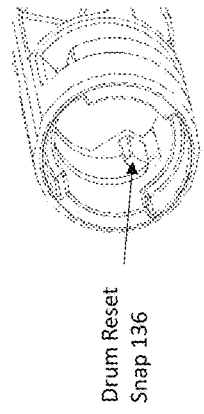
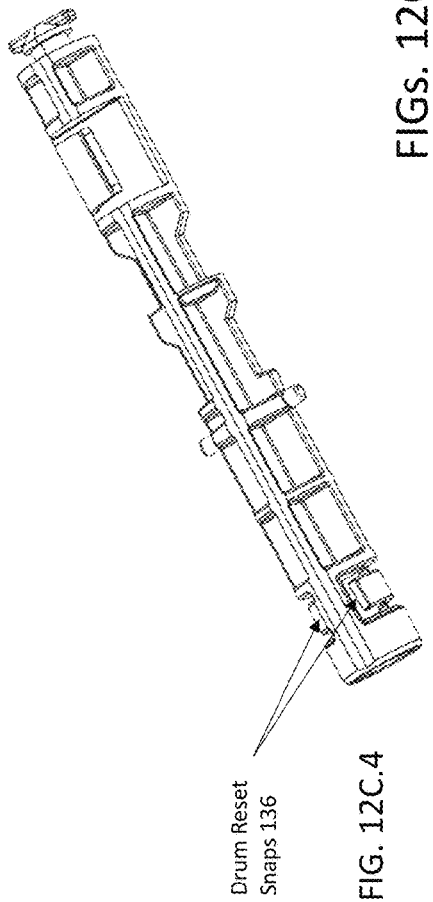
FIGs. 12C.1-5

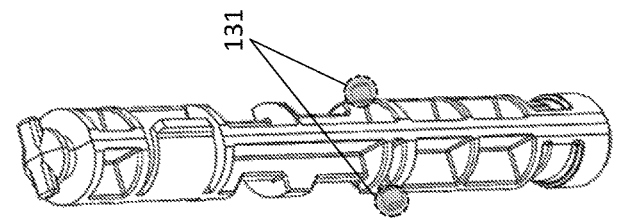
FIG. 12D.4
FIG. 12D.3
Path of Drum Protrusion in Trigger Assembly Pathway during Cap/Drum rotation. Trigger assembly can now move axially.
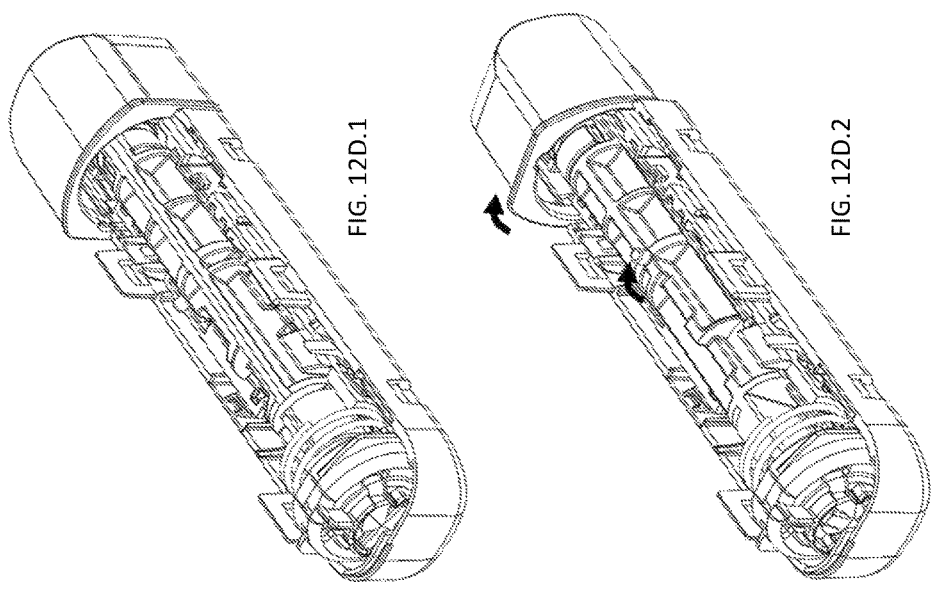
FIG. 12D.1
FIG. 12D.2
Rotation of Drum with CAP
UI1: User Twists Cap
1.1b, 1.2b

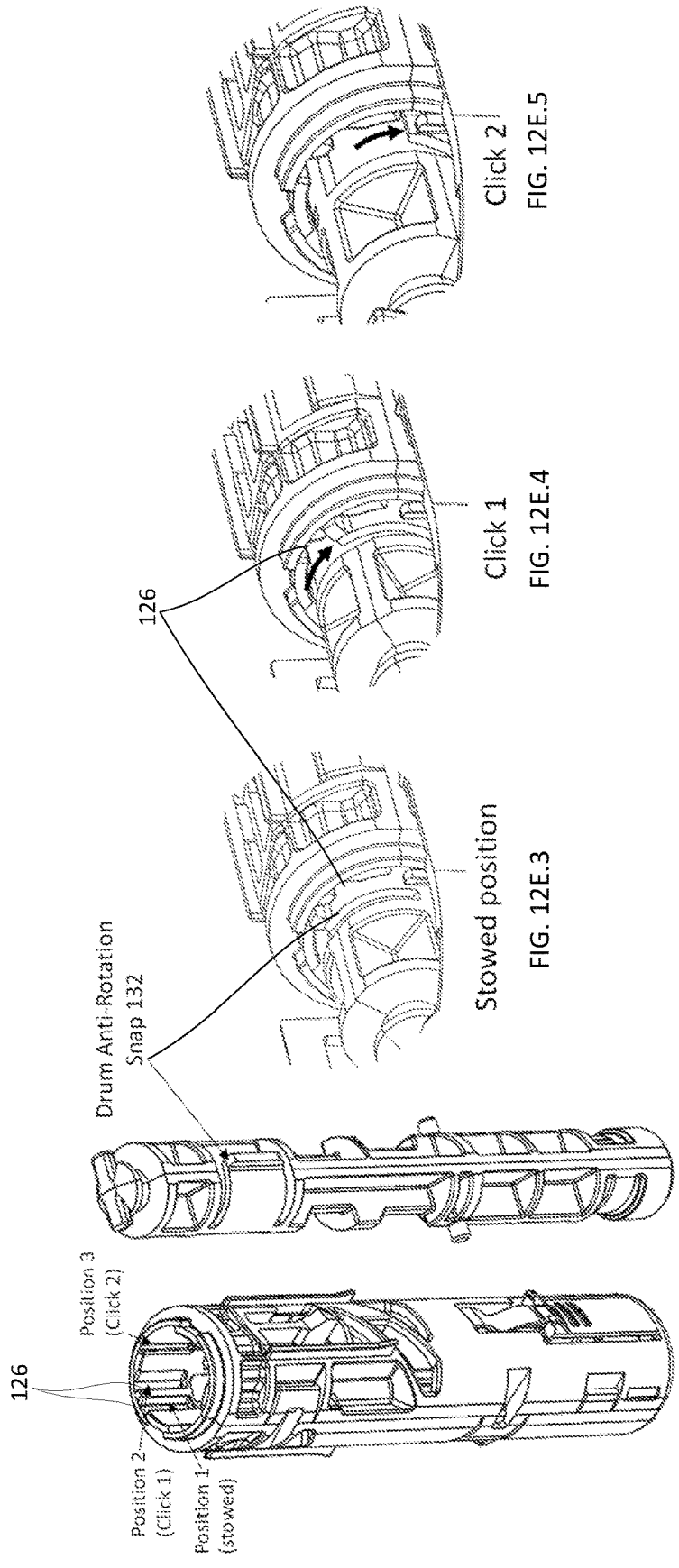

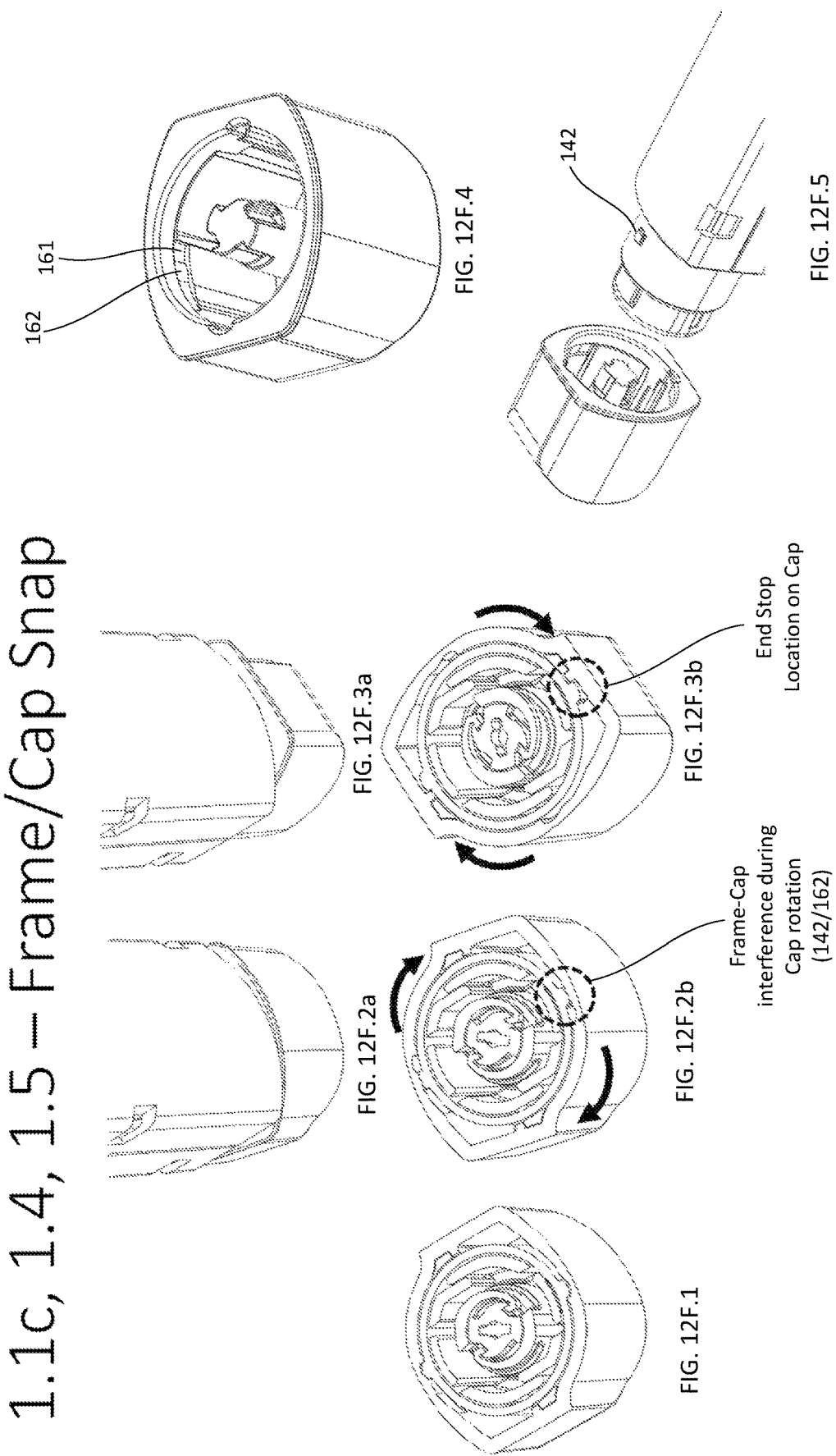

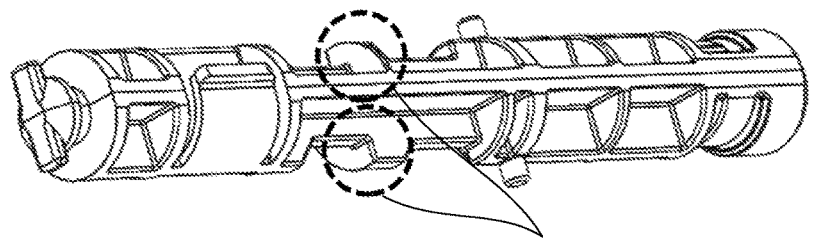
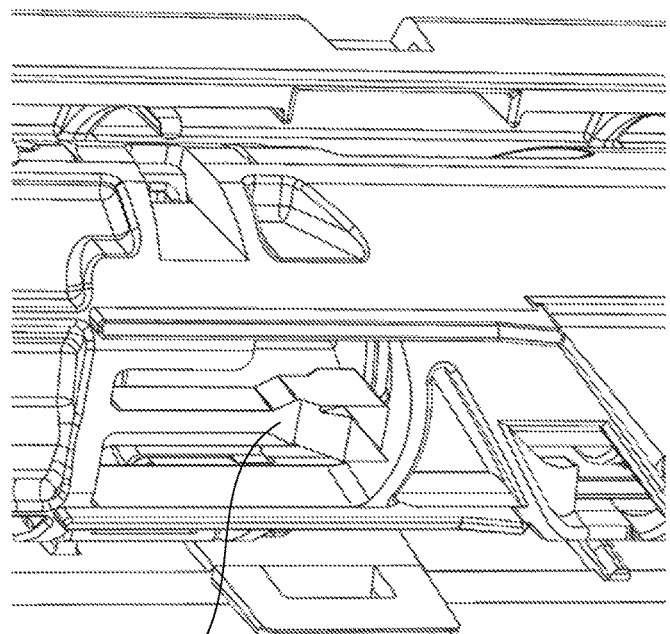
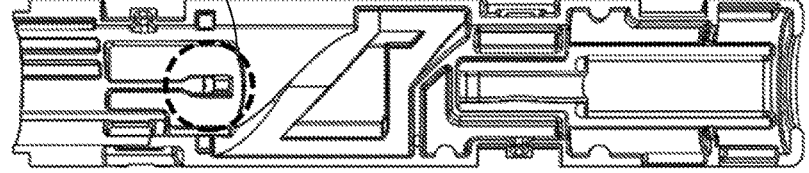
FIG. 12G.1  FIG. 12G.2  FIG. 12G.3

S1: Primed State

UI3: User Presses Trigger Assembly to Thigh

UI3: User Presses Trigger Assembly to Thigh
2.1b, 2.2b Housing Ramping Feature
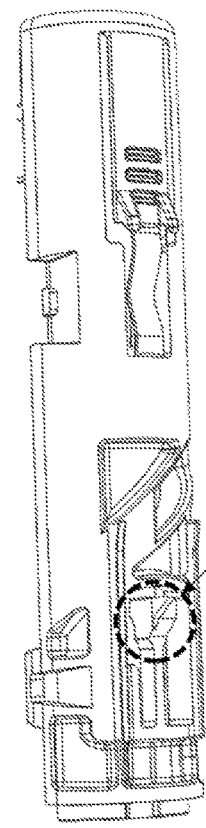
FIG. 12K.3
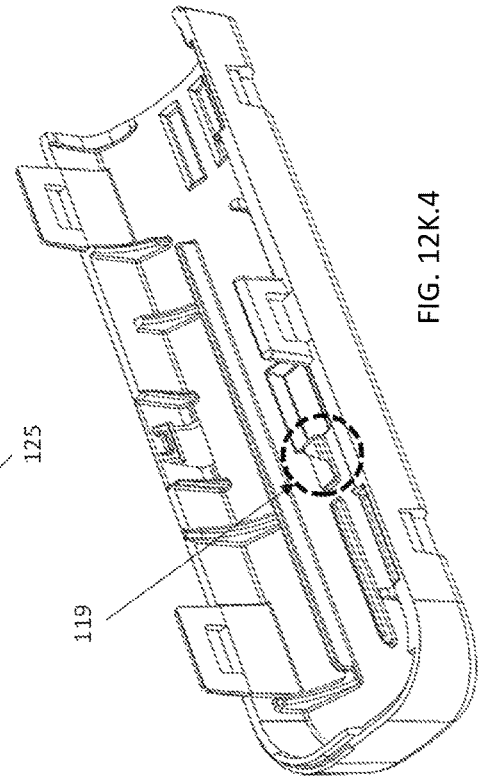
FIG. 12K.4
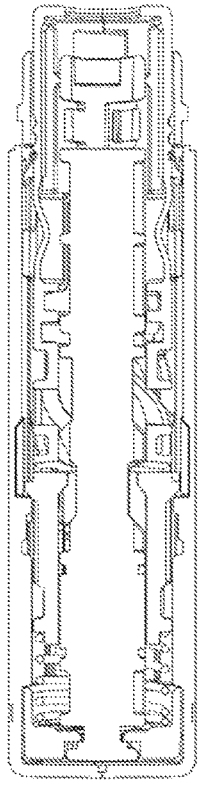
FIG. 12K.1
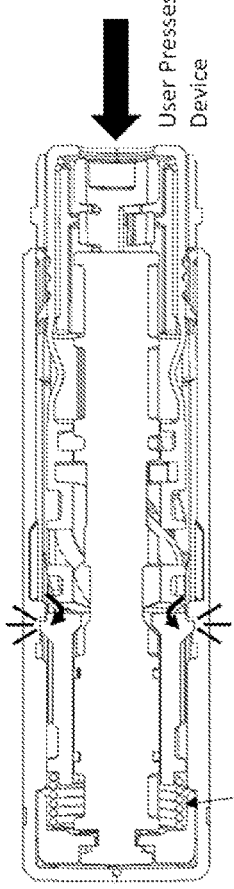
FIG. 12K.2
User Presses Device
TA two-way snap 125 Clicks after moving up and over Housing Ramp Feature 119.
Spring 152 compresses

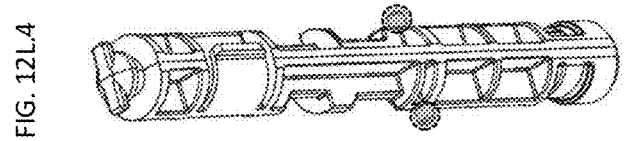
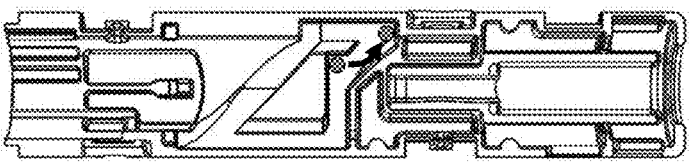
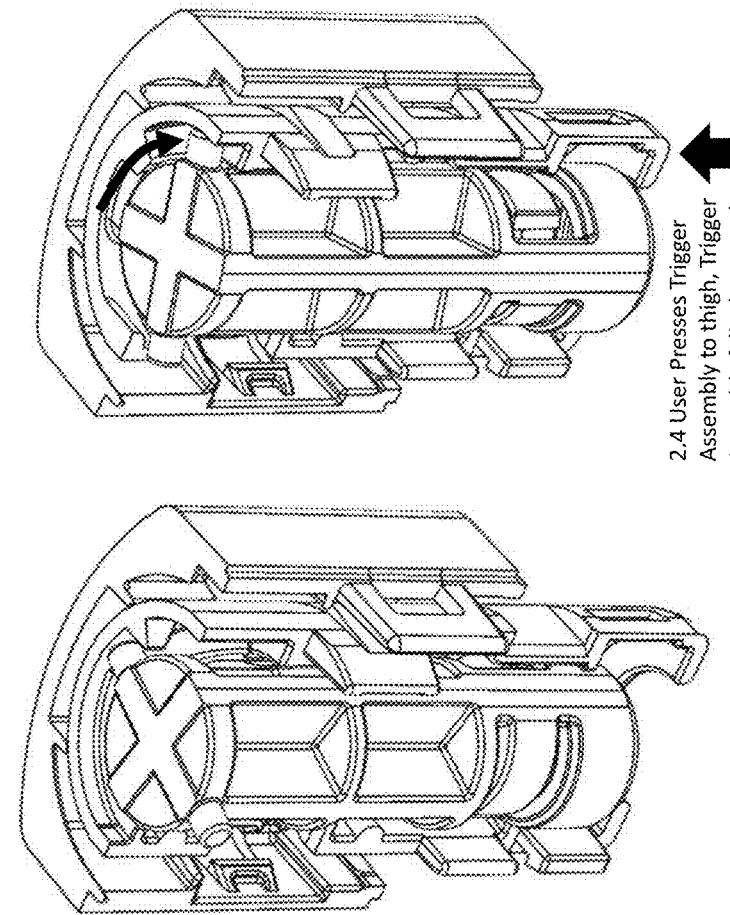

S2: Activated State

UI5: User removes device from thigh

UI5: User Removes device from thigh
3.1 Spring extends Trigger Assembly upon removal
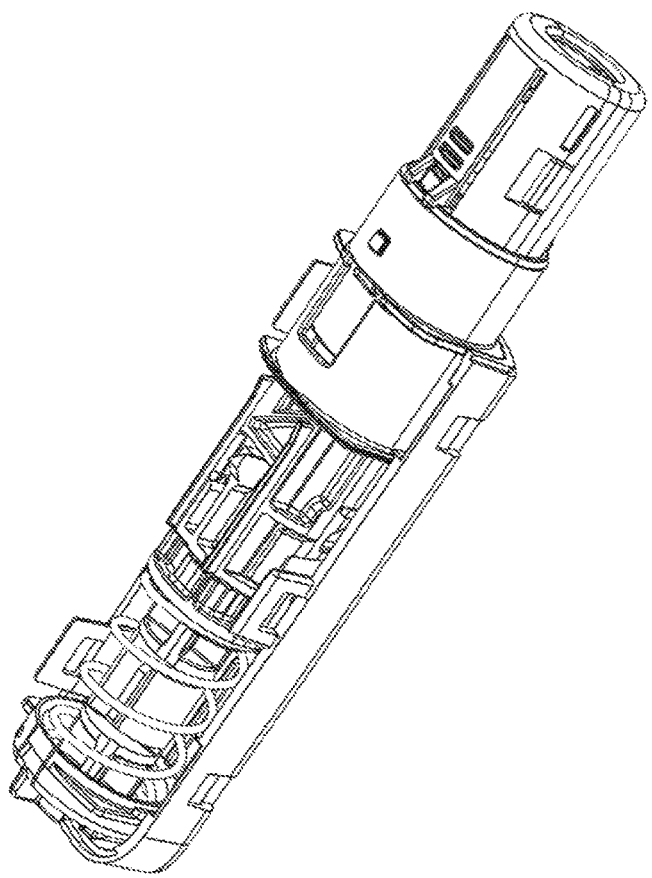
FIG. 12P.2
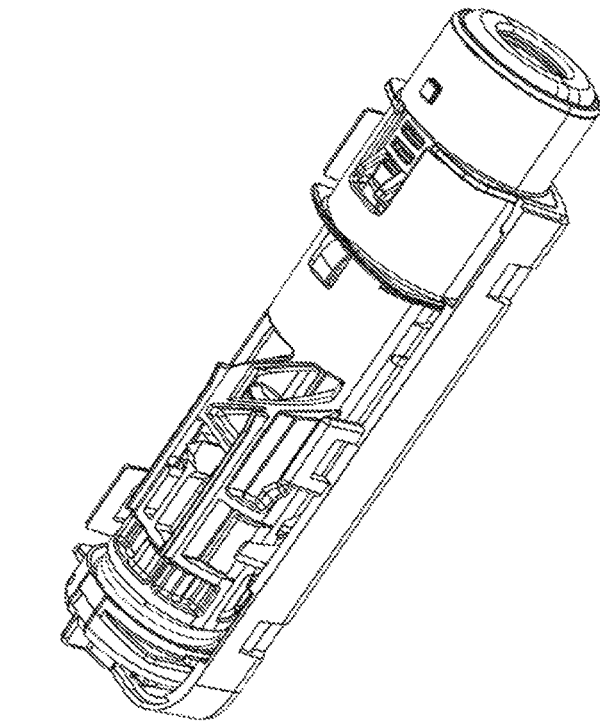
FIG. 12P.1

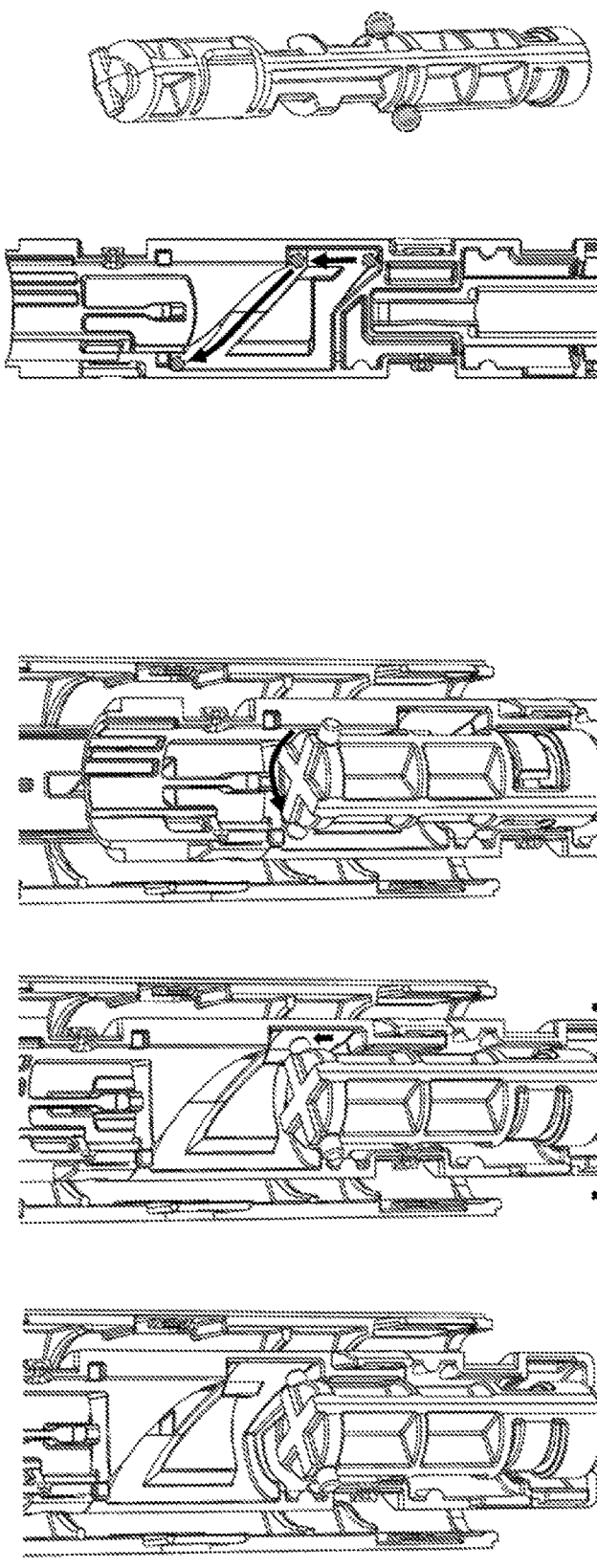

3.2b TA Snap bypasses Housing Ramp Feature
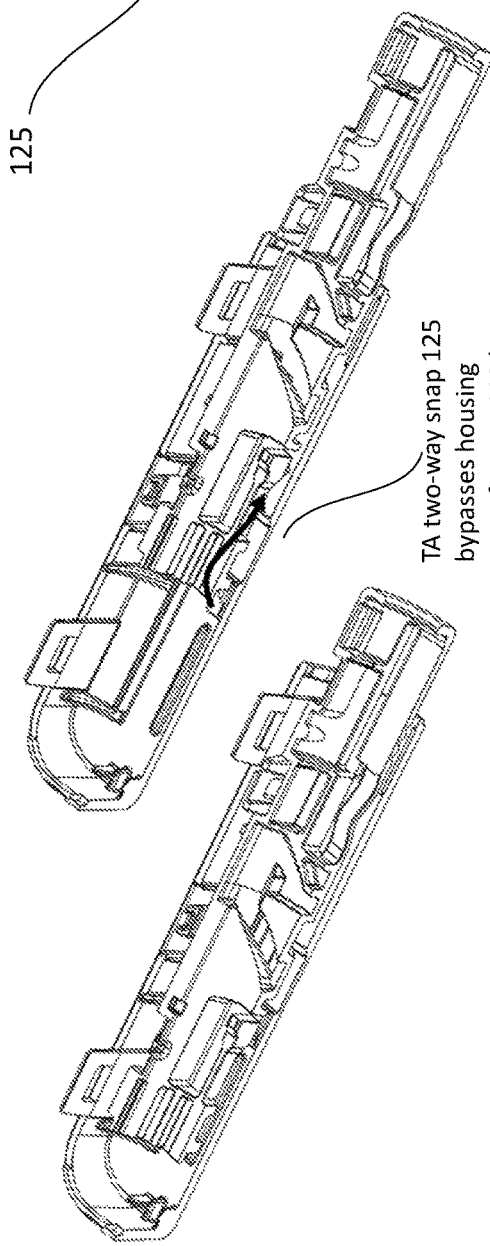
FIG. 12R.1
TA two-way snap 125 bypasses housing ramp feature 119 by flexing sideways.
FIG. 12R.2
FIG. 12R.3
FIG. 12R.4

UI5: User Removes device from thigh
3.3,3.4 NS Lockout Tabs
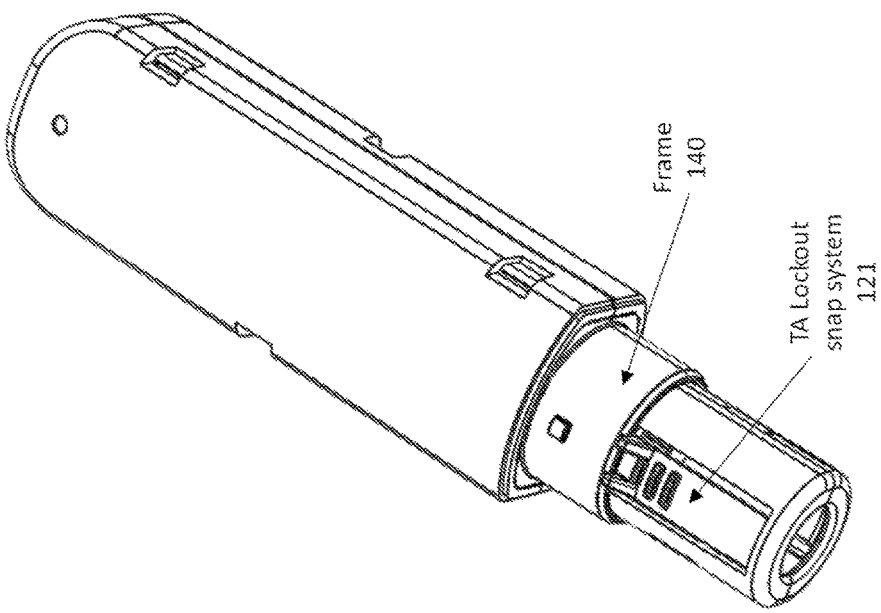
FIG. 12S.3
FIG. 12S.1
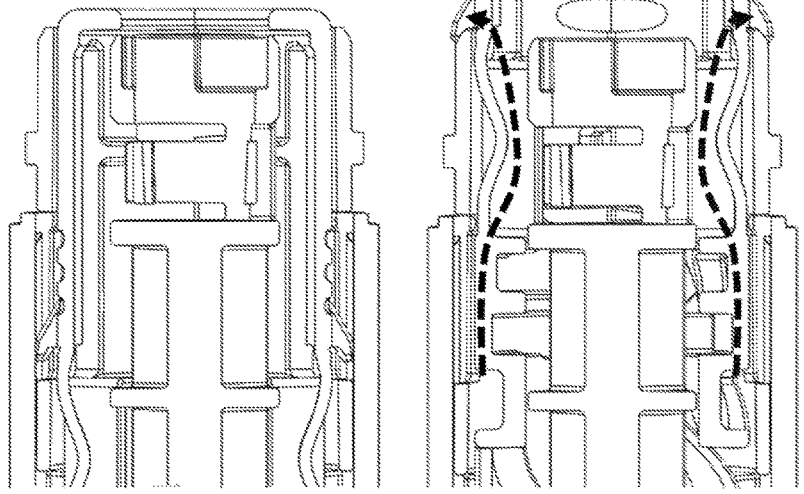
Lockout tabs 122 flex inward and then outward once clear of frame.
Cross-section view showing TA lockout tabs 122 travel pathways during TA extension.
FIG. 12S.2

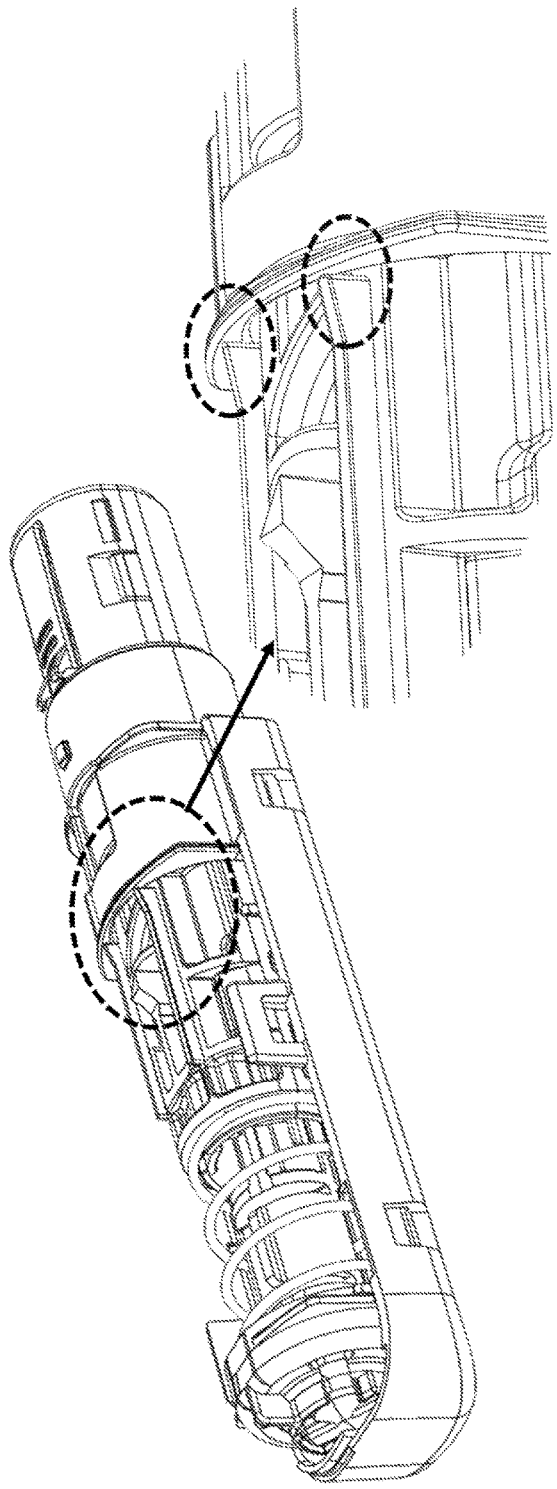

S3: Lockout State

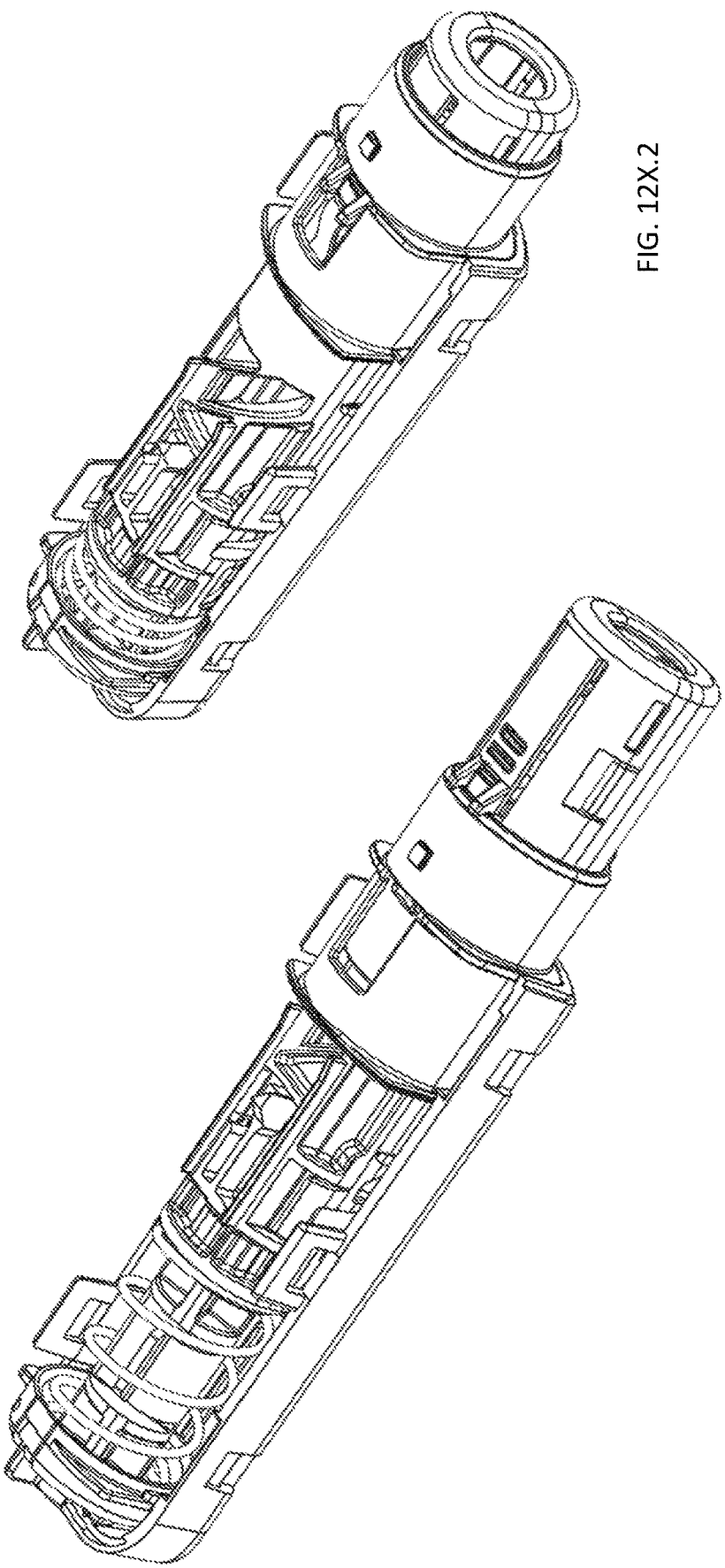
FIG. 12X.2
FIG. 12X.1

UI7: User Presses TA to stowed position
4.4 TA Snaps engage with Drum, makes clicking sound, TA retained
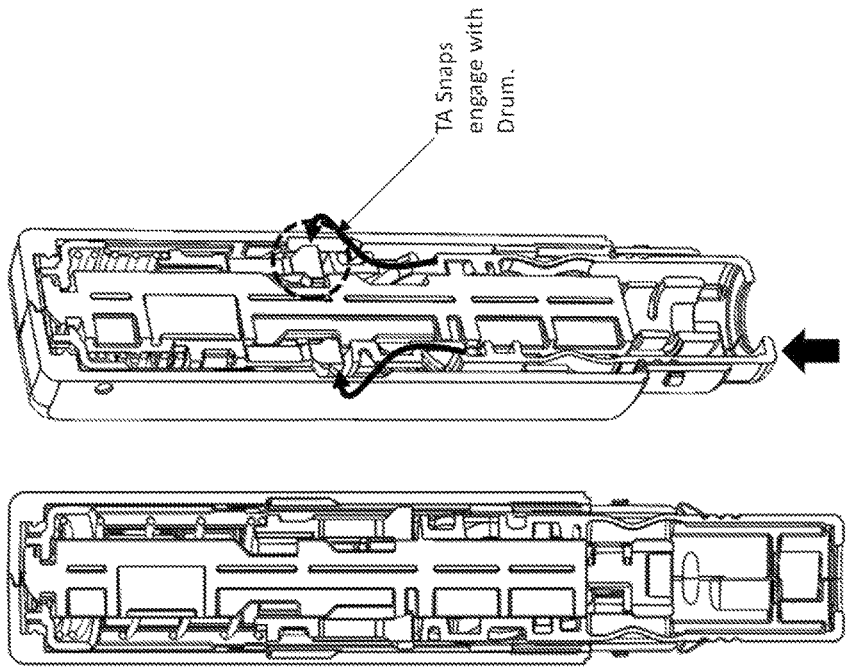
FIG. 12Z.1
FIG. 12Z.2

UI8: User replaces Cap 4.5 Cap Gear/Spline aligns with Drum Reset Snaps

4.6 Cap contacts frame at end of axial travel

UI9: User rotates cap clockwise to stowed position
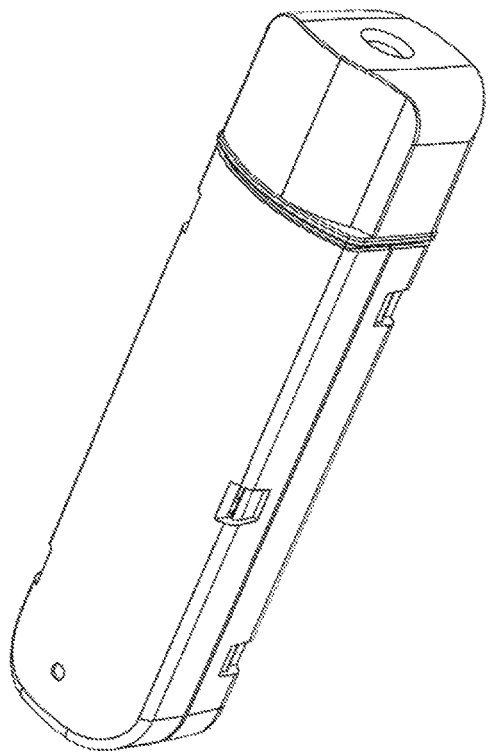
FIG. 12DD.2
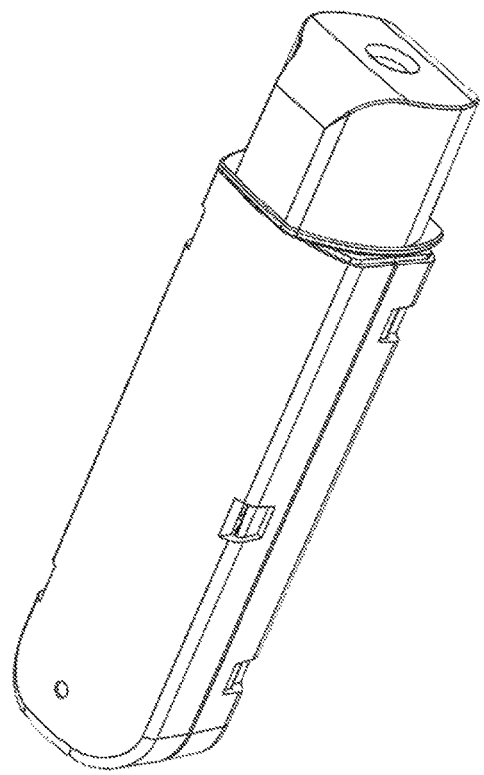
FIG. 12DD.1
FIG. 12DD.1-2

4.8 Cap gear passes by Drum Reset Snap, makes clicking sound 4.9 cap over-rides Frame Protrusion makes clicking sound 4.10 Cap reaches end of travel contacting Frame Protrusion

AUTOINJECTOR TRAINING DEVICE

RELATED APPLICATIONS

This application claims the benefit of U.S. Provisional Patent Application No. 62/906,879 filed on Sep. 27, 2019; which is herein incorporated by reference in entirety.

TECHNICAL FIELD

The present invention generally relates to training devices, and particularly relates to training devices designed to teach users how to use an injector and/or autoinjector device.

BACKGROUND

In the medical field and particularly when a stressful situation arises errors can often occur when treating another person or patient. As a result, it is common to practice how one will respond in given situations. For example, CPR training has gone on for decades, and the trainings have been updated over the years as new techniques have been implemented. For example, compact portable AED devices are a fairly new device in the field of CPR and their proliferation into schools, churches, amusement parks and so forth is even newer. As a result, CPR trainings have been modified to familiarize users with the devices and how to operate them should the need arise.

Certain types of autoinjectors have existed and been used for several years; however, new innovations to autoinjectors have been recently developed, which include devices that are of different sizes and have different functionality. E.g. the ability to instantly mix upon activation. Therefore, there is a need to develop more accurate training devices to mimic the real use of these newer types of autoinjectors in the market; thus, helping reduce user error.

SUMMARY

In one embodiment an injector training device comprises a housing 110; a trigger assembly 120 at least partially disposed within the housing; and a drum assembly 130 at least partially disposed within the trigger assembly, wherein the drum assembly has at least one drum protrusion 131 configured to engage a drum protrusion channel 123 formed in a sidewall of the trigger assembly.

The drum assembly can further include anti-rotation snaps 134 configured to correspond to at least one recess 126 formed in the sidewall of the trigger assembly. These anti-rotation snaps 134 are configured to allow the drum to rotate in one direction.

The drum assembly can further include at least one drum reset snap 136 that is configured to interface with a portion of a cap 160, and in particular the spline 164 extending into the cavity portion 168 of the cap. The spline is formed to interface with the drum reset snap such that rotating one direction, allows the reset snap to bend outwards and make a snap or clicking noise, while rotating the spline the opposite direction engages the reset snap and depending on the state of the drum assembly causes the drum assembly to rotate within the trigger assembly.

The injector training device can further include a frame 140 disposed over the trigger assembly. The frame can include at least one frame protrusion 142 that interfaces with an inner protrusion 162 of the cap and wherein the interface between the inner protrusion and the frame protrusion creates an interference force when rotating the cap with respect to the housing.

The anti-rotation snaps 134 cause a clicking sound when the drum assembly is rotated with respect to the trigger assembly. The anti-rotation snaps can also cause a second clicking sound when the drum assembly is rotated further with respect to the trigger assembly. Each of the clicking sounds generated are indicative of similar sounds generated by an injector device that delivers mixed medicament components.

The housing 110 can formed of two interlocking housing components 110a, 110b.

Similarly, the trigger assembly 120 is formed of two interlocking needle shield components 120a, 120b.

A spring retainer 150 configured to hold a spring 152 in place between the spring retainer and the trigger assembly 120 can be disposed within the housing. Actuating the trigger assembly causes the spring to extend the trigger assembly in an activated state.

The trigger assembly can further include a lockout snap system 121 to prevent the trigger assembly once activated.

The trigger assembly can further include a two-way snap element 125 that interfaces with a ramp feature 119 of the housing in two separate planes and causes a snapping or clicking sound when the two-way snap bypasses the ramp feature in a first plane or a second plane.

The drum assembly can also include a t-connector 135 that interferingly engages the spring retainer.

In another embodiment the injector training device comprises a housing 110;
  a cap 160 having an inner protrusion 162 disposed on an interior sidewall of the cap; a trigger assembly 120 at least partially disposed within the housing; and a drum assembly 130 at least partially disposed within the trigger assembly, wherein the drum assembly has at least one drum protrusion 131 configured to engage a drum protrusion channel 123 formed in a sidewall of the trigger assembly, wherein the drum protrusion channel forms part of a drum protrusion pathway 124.

The trigger assembly 120 that is at least partially disposed within the housing becomes accessible upon removal of the cap.

A complete cycle of the drum protrusion through the drum protrusion pathway causes the training device cycle from a stowed state, to a primed state, to an activated state, to a lockout state, and back to the stowed state.

A method for training a user how to use an injector device, can include using the injector training devices described above and comprise the steps of:
  rotating the cap with respect to the housing, until notches of the cap are aligned with the at least one frame protrusion;
  removing the cap from the rest of the injector training device, thus transitioning the injector training device from a stowed state to a primed state, and whereby the trigger assembly is now exposed;
  pressing the exposed trigger assembly against a body portion, thus transitioning the injector device from a primed state to an activated state;
  holding the depressed trigger assembly against the body portion for a period of time;
  removing the injector training device from the body portion, thus transitioning the injector training device from an activated state to a lockout state, whereby the trigger assembly is extended outwardly from the housing;

depressing inwardly a lockout snap system formed into the trigger assembly;

axially depressing the trigger assembly into the housing;

placing the cap back onto the injector training device, by aligning the notches with the at least one frame protrusion; and rotating the cap until it aligns with the housing, whereby the injector training device returns to the stowed state.

BRIEF DESCRIPTION OF THE DRAWINGS

FIGS. 11A-E is a diagram of the steps involving user interaction, processes and states associated with an injector training device.

DETAILED DESCRIPTION

Figure 1A:
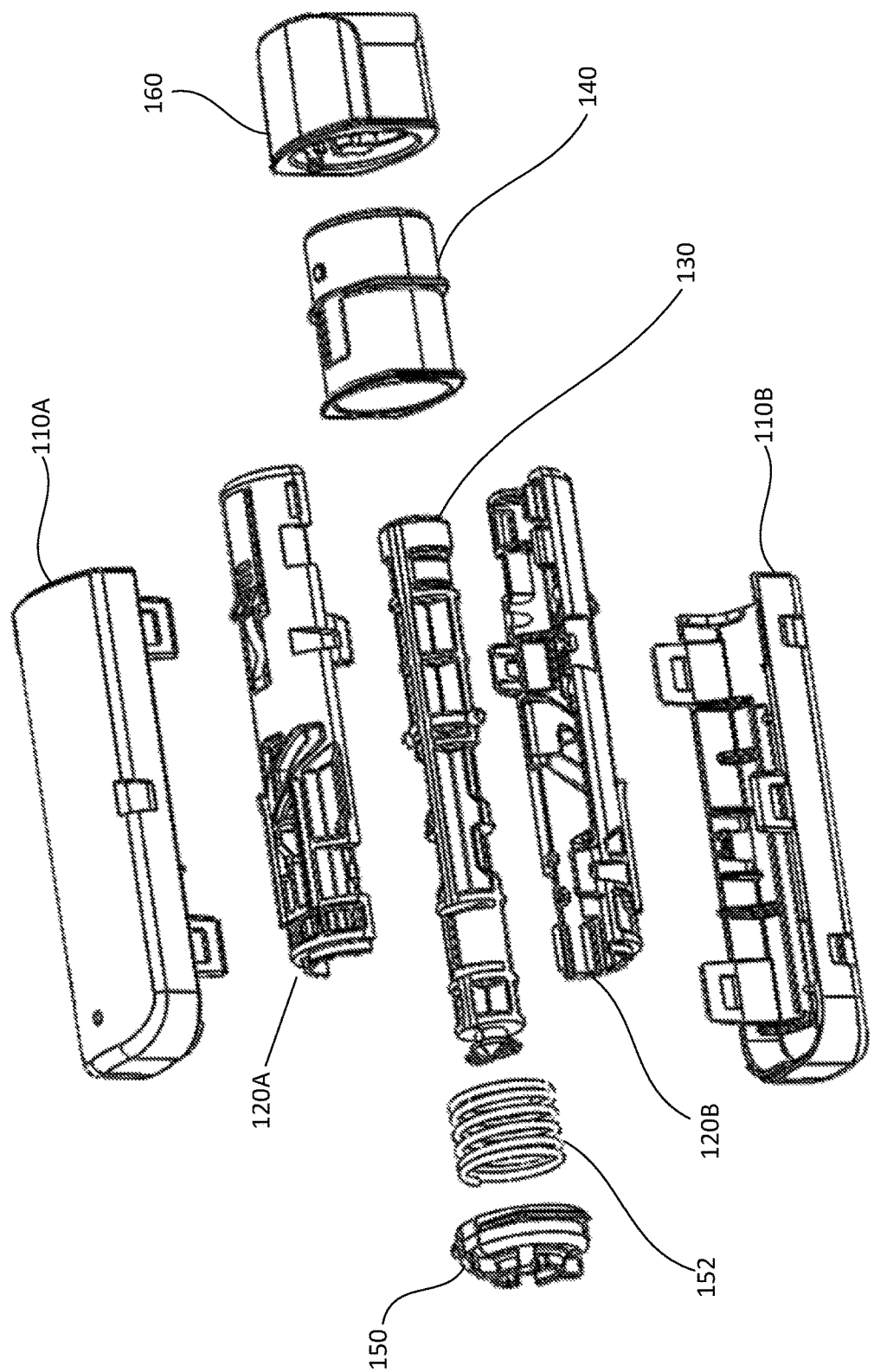
FIG. 1A is an exploded perspective view of an autoinjector training device.
Figure 1B:
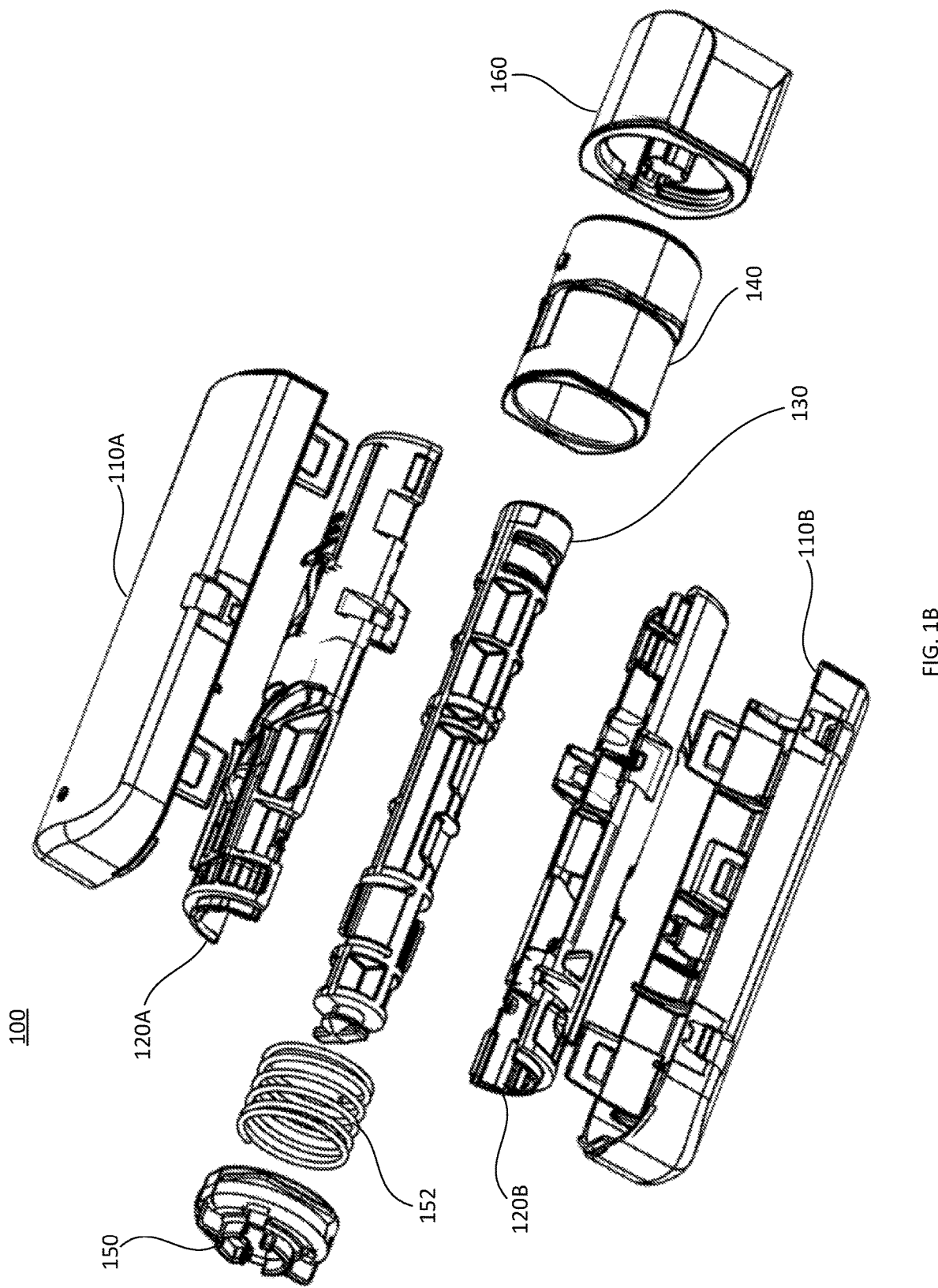
FIG. 1B is another exploded perspective view of the injector training device of FIG. 1A.
Figure 1C:
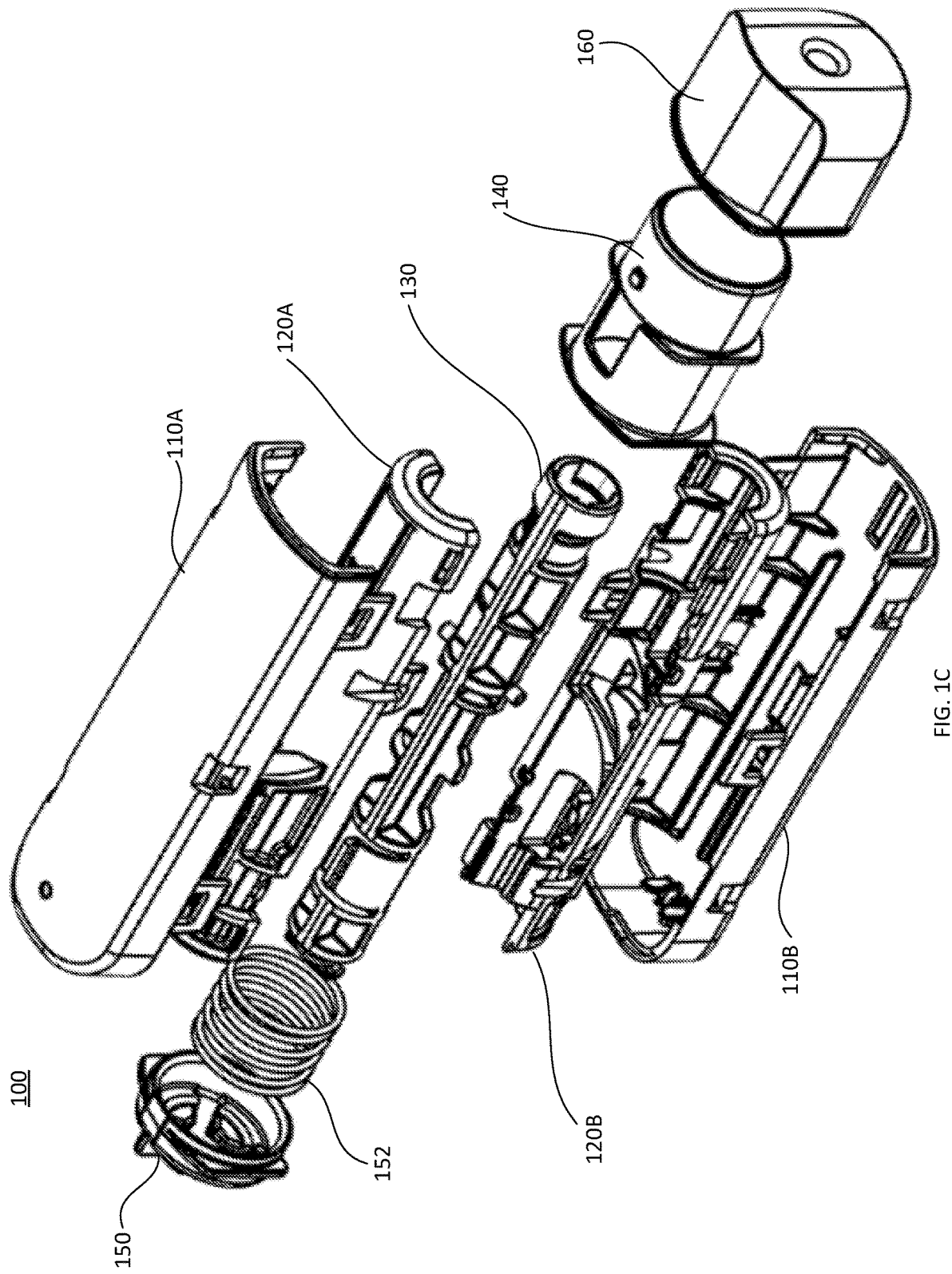
FIG. 1C is yet another exploded perspective view of the injector training device of FIG. 1A.
Figures 1D, 1E:
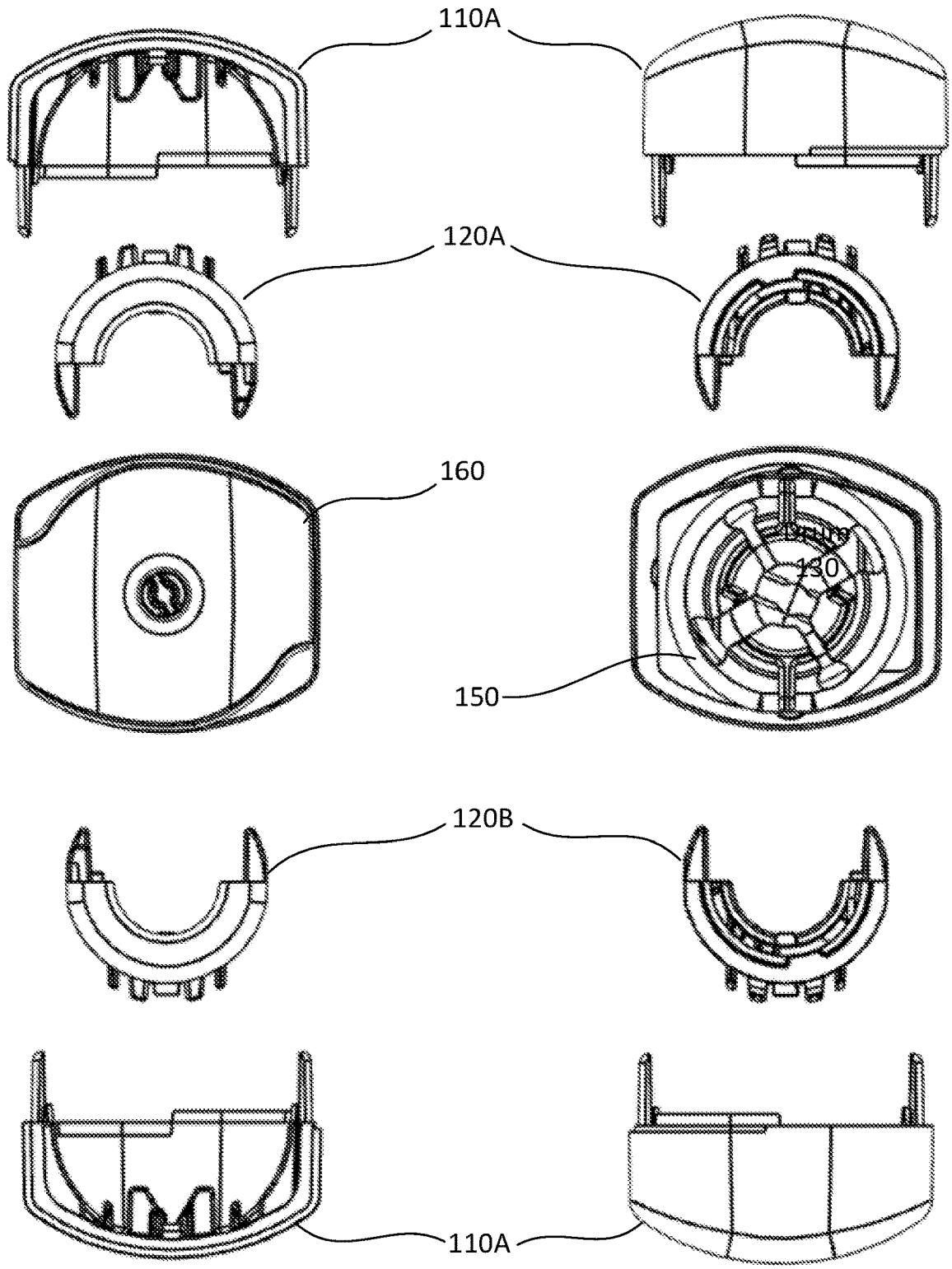
FIGS. 1D-E are exploded top and bottom views of the injector training device of FIG. 1A.
Figure 2A:
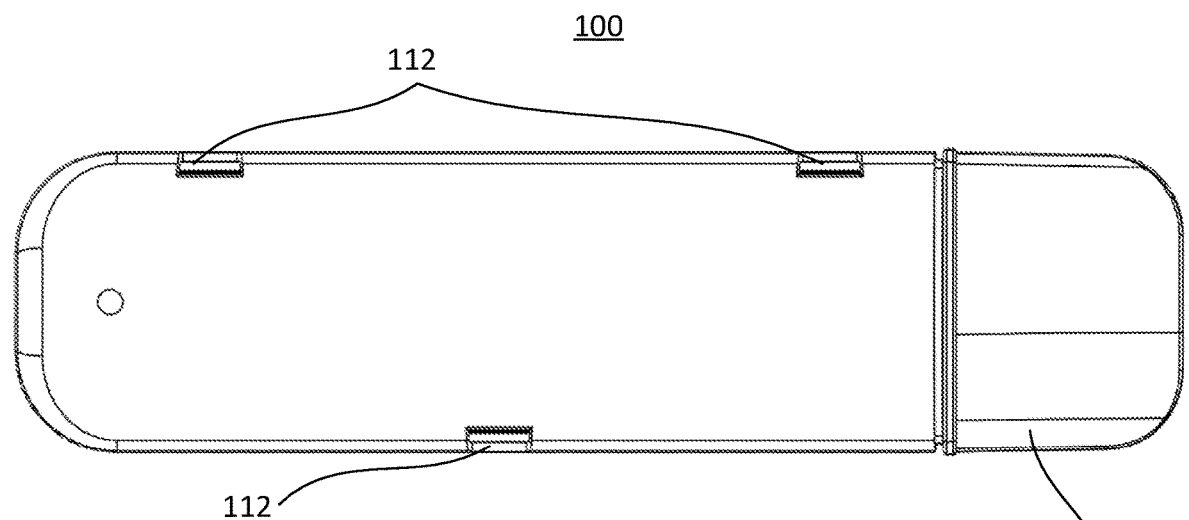
FIGS. 2A-E are various views of the injector training device outer housing and cap including front, left, top, bottom and perspective views.
Figure 2B:
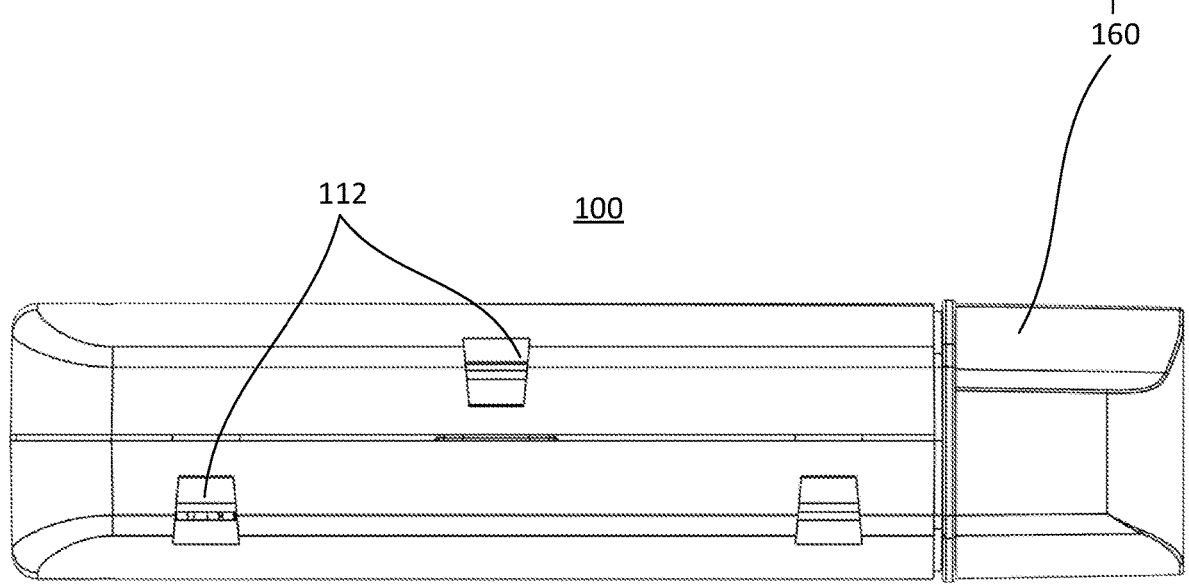
Figure 2C:
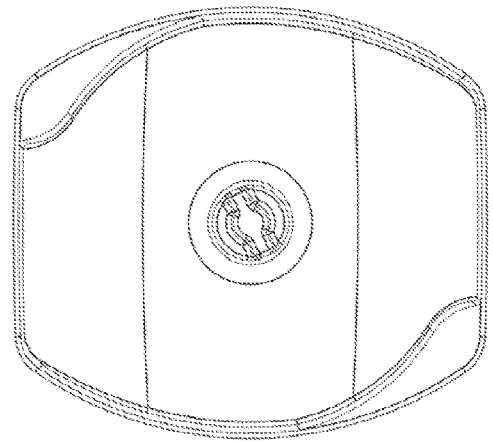
Figure 2D:
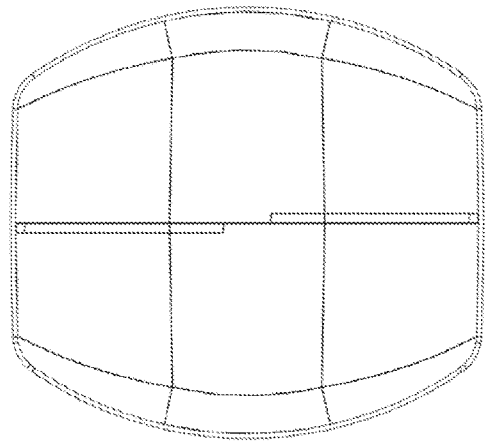
Figure 2E:
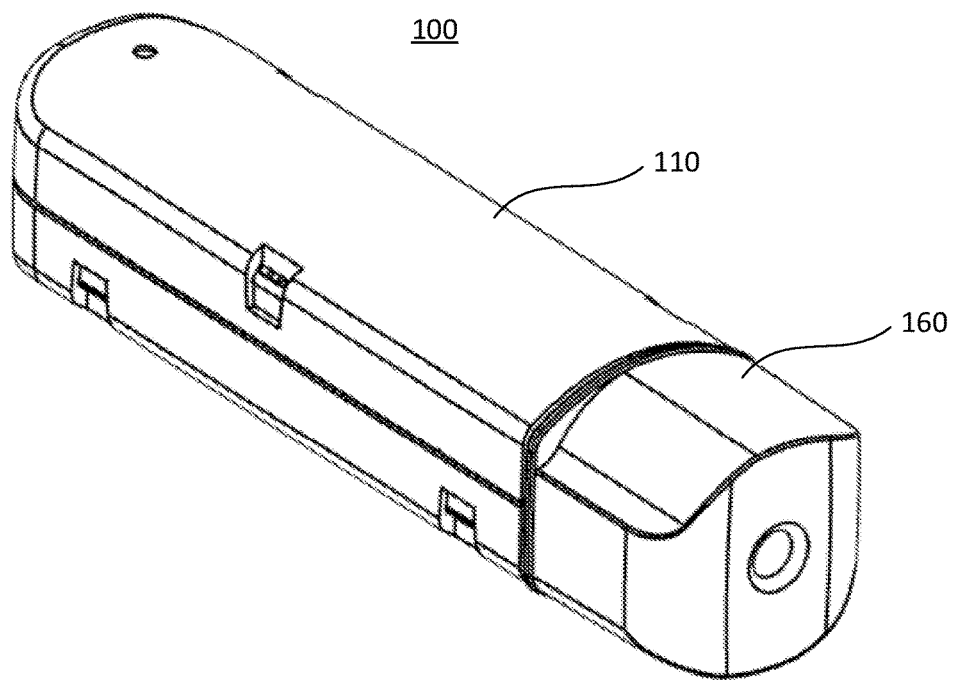
Figure 3A:
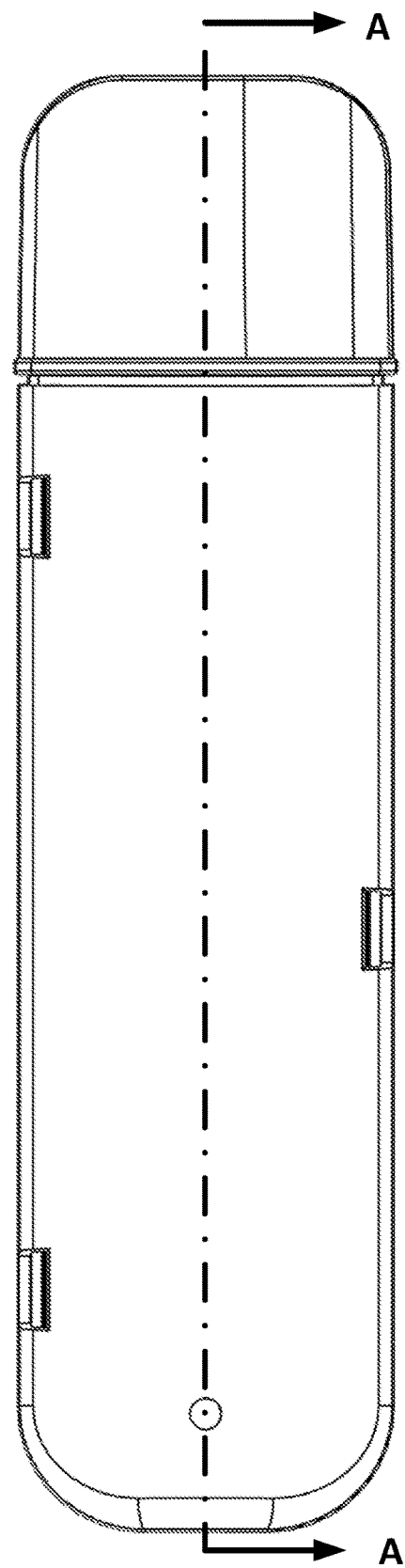
FIGS. 3A-B illustrate a cross-sectional view of the injector training device.
Figure 3B:
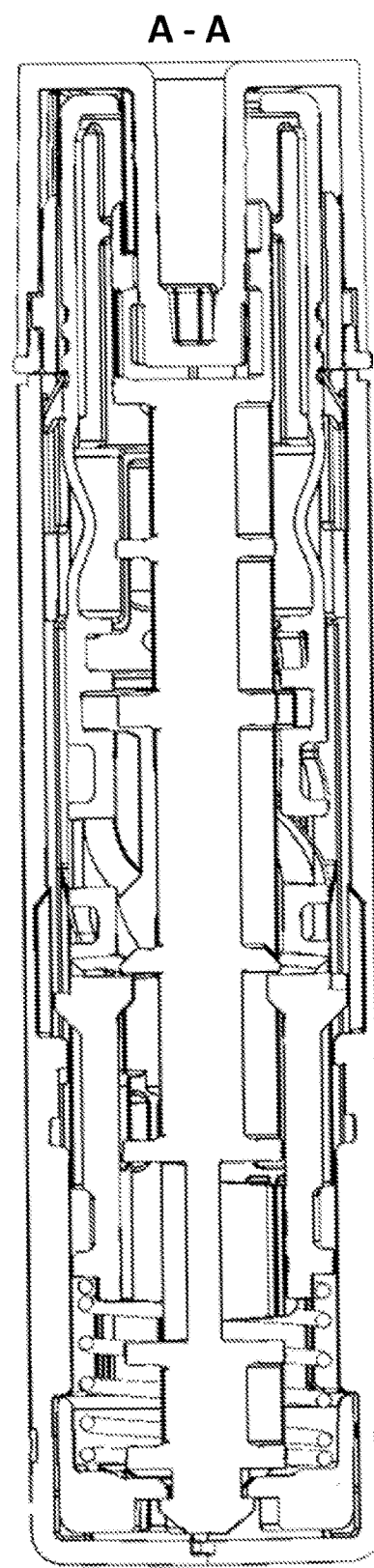
Figure 4A:
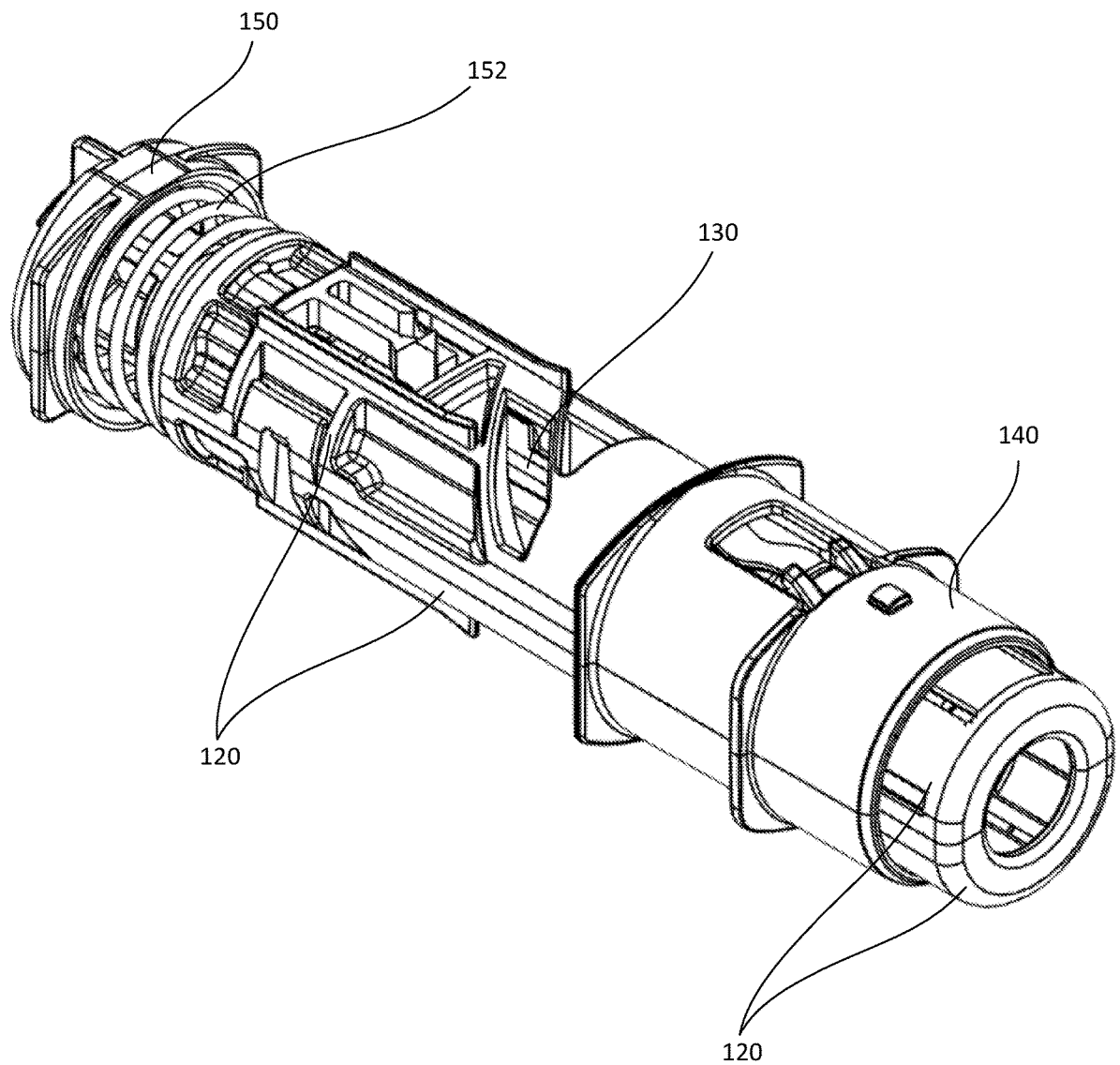
FIG. 4A is a perspective view of the injector training device without the housing and cap.
Figure 4B:
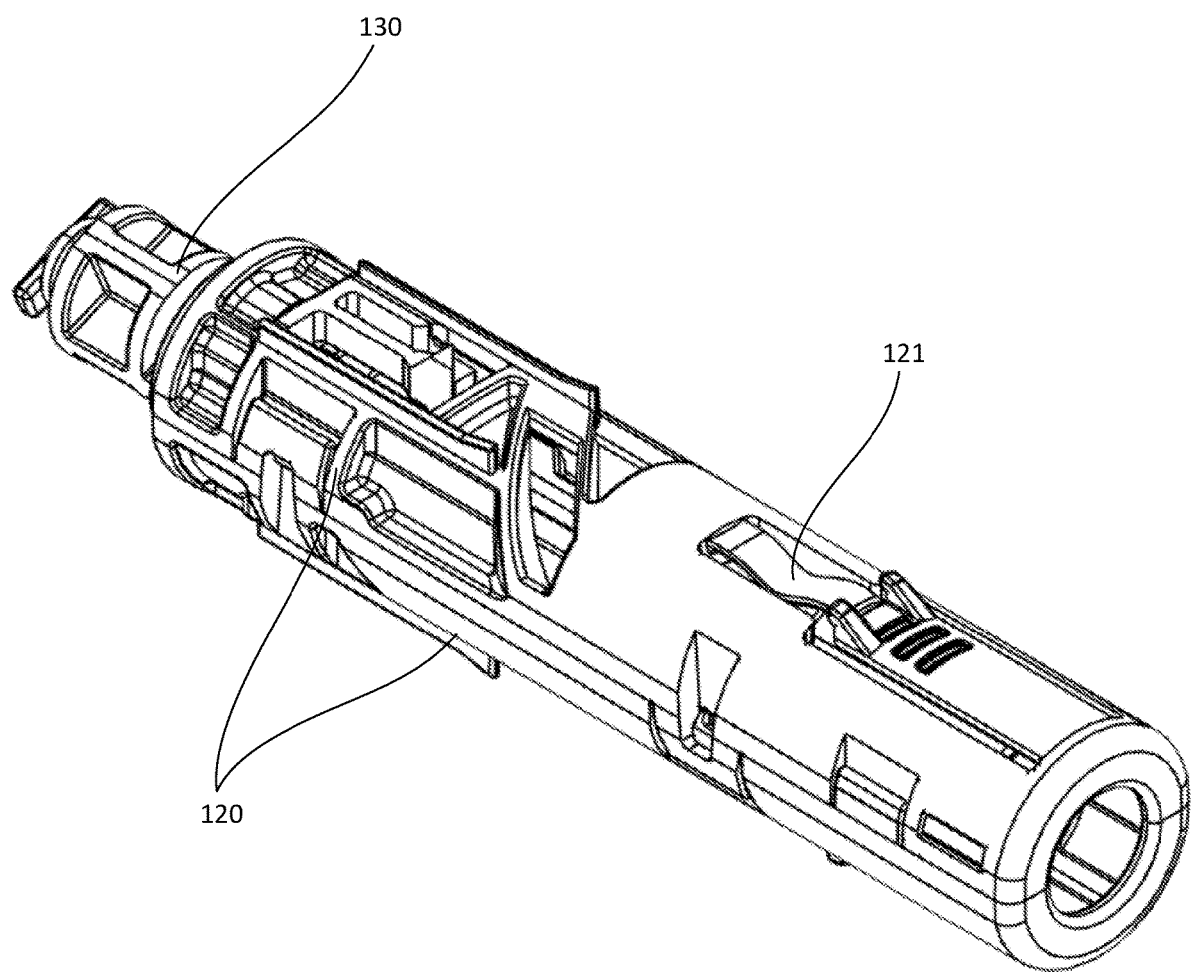
FIG. 4B is a perspective view of the injector training device without the housing, spring retainer, spring, frame and cap.

As noted, the embodiments and features described herein are designed for the purposes of helping training persons how to use an injector and/or an autoinjector device such as the one described in U.S. Pat. No. 10,300,198 a Portable Drug Mixing and Delivery Device, which includes first and second chambers each having medicament component that mix upon actuating the device and then delivers the mixed medicament upon depressing a trigger feature that injects a needle into a person and causes the mixed medicament to flow from the second chamber into the person through the needle.

Many of the medicaments contemplated being used in the autoinjector mentioned above are often utilized in high stress situations. For example, epinephrine is utilized to help stabilize persons going into anaphylactic shock generally as a result of consuming something they are highly allergic to or alternatively being stung by a bee or insect. This type of situation tends to be stressful as noted, thus providing a need for a training device configured to be utilize for a potential real administration of an autoinjector device having epinephrine. Another high-stress situation uses naloxone, nalmefene, or other opioid antagonist medicament in a mixing and delivery autoinjector device. Again, when a person has overdosed on opioids and is in non-responsive or controllable state, autoinjectors rapidly mixing and delivering these types of drugs can help the person stabilize to where additional assistance can be had. Another drug called Glucagon is a hormone that is involved in controlling blood sugar. Persons who need assistance controlling blood sugar and insulin levels may need to inject glucagon into their system to assist with this regulation. This drug can even be administered when a person has fallen unconscious as result of not managing sugar and insulin levels. Again, this can be another high-stress situation where appropriate training from a training device configured to mimic a glucagon autoinjector system can help reduce stress and potentially save a life. The embodiments and methods below can be adapted for autoinjectors configured with epinephrine, opioid antagonists, and glucagon, as well other drugs used in other high-stress situations. It should also be noted that even in non-high-stress situations administering a drug via a needle of an autoinjector if not done correctly can be problematic, so other drugs can also be utilized and practiced using the training devices and methods described below.

As shown in FIGS. 1A-12GG are various views, diagrams and uses of an injector training device. The various features are listed below and the operations are described in the diagrams and shown in the figures. Many of the features of the embodiments shown are intended to mimic a real working autoinjector mixing and delivery device. For example, the frame protrusions 142 interfacing with the inner cap protrusions 162 are configured such that as the cap rotates an amount of pressure or force is require to rotate through the interference caused. This amount of pressure or force to be overcome is designed to mimic the rotational forces necessary twist the cap on an injector device, and/or to tear a safety seal, such as a sticker or label, that runs across the body of the device to the cap. In order to break or tear the seal when rotating the cap, a user will need to use some additional force. Thus, the frame protrusions and inner cap protrusions provide this ability to mimic what would be felt by the user operating a real injector device as closely as possible. In another embodiment the forces in the training device may exceed the types of forces experienced in the actual injector device. This may be done to ensure the user is trained to overcome some minimum force so when it's time for the real device to be used the user can be reasonably expected to apply a sufficient force to twist the cap. This kind of haptic or pressure feedback can be tuned to allow for a better training device.

Other features include various anti-rotation features with tabs that cause clicking noises as they pass from recess to recess in the trigger assembly. These clicking noises and haptic feel again are design to mimic the sounds and feel of an actual injector and/or autoinjector device as described above as it is actuated to mix the medicament components and prepared for injection.

LABELED ELEMENTS OF THE DRAWINGS

100—injector training device
110—housing
110a—housing component
110b—housing component
112—notches
113—tabs
114—attachment features
115—guide ribs
116—cross ribs
117—guide ribs distal end
118—guide ribs proximal end
119—ramp feature
120—trigger assembly
120a—trigger assembly component
120b—trigger assembly component
121—trigger assembly lockout snap system
122—lockout snap protrusions
123—drum protrusion channels
124—drum protrusion pathway
125—two-way snap element
126—trigger assembly snap recesses
127—two-way snap angled edge
128—two-way snap ramp
129—trigger assembly guide rail
130—drum assembly
131—drum protrusion
132—drum anti-rotation snap
133—anti-rotation snap tab feature
134—anti-rotation snap flex arm
135—drum t-connector
136—drum reset snap
137—reset snap angled protrusion
138—upper drum cavity
140—frame
142—frame protrusion
144, 146—frame flanges
148—frame aperture
150—spring retainer
151—retainer cross aperture
152—spring
153—retainer flange
155—retainer guide
157—retainer stop
159—retainer cavity
160—cap
161—inner recess
162—inner protrusion
163—recess ledge/flange
164—spline
165—cap flange
166—cap flange notch
167—spline elements
168—cavity portion of the cap (NOT LABELED)

Referring now to FIGS. 1A-E and 2A-E are shown an exemplary injector training device 100 comprised of the following components and assemblies, namely housing 110, trigger assembly 120, drum 130, frame 140, spring retainer 150, spring 152 and cap 160.

Housing 110 as shown can be comprised of two housing components 110A and 110B. Housing Components 110A and 110B as shown in the embodiment shown herein are identical, however, it is well understood that these components do not have to be identical. One of the advantages of being identical is on the manufacturing side, where a single mold can be made. Assembly of the components is also simplified in that any two of the components can be assembled together to form housing 110. FIGS. 5A-E illustrate housing component 110B and the various features that interface with housing component 110A, the trigger assembly 120, spring retainer 150, frame 140 and cap 160. Drum 130 is primarily disposed within the trigger assembly 120 and thus does not interface directly with the housing, although the components work together to accomplish the purpose of the injector training device 110, which is mimic a real autoinjector mixing and delivery device, so as to train users how to appropriately use the real autoinjector device as noted above.

As shown in FIGS. 5A-E two tabs 113 are formed along one side of the housing component 110B and a third tab is formed on the opposite side. Each of these tabs 113 are formed along an inner sidewall of the housing component 110B. Corresponding notches 112 are formed next to each of the tabs 113. The tabs 113 interface with corresponding attachment features 114. 114 is pressed into each corresponding tab 113, which can have an angled surface that allows the attachment feature 114 to flex inward and once passing the tab, snap back into place, where the tab is inserted into and affixed by an aperture of attachment feature 114. The notches allow the attachment features to be pressed inward once attached, to enable a release of the attachment feature from the tab, thus removing the housing components 110A and 110B from each other. It should be understood that the notches are not necessary and can be removed, where 113 and 114 will still perform the desired function of securing housing components 110A and 110B to form housing 110.

Other features of the housing component 110B include guide ribs 115 and cross ribs 116. These various ribs allow the trigger assembly when inserted to the housing, to rotate and translate axially through the various actuation steps that mimic a real injector device, as later shown and described in FIGS. 11A-e and 12A-GG. The guide ribs 115 have a distal end 117 and a proximal end 118. There is a gap between 117 and the last cross rib 116 on the distal end of the housing component 110B. This gap is sized to allow frame flange 144 of the frame 140 to be disposed therebetween and fix it into place to prevent any axial movement. The frame flange is also formed to correspond in shape to the inner sidewalls of the housing component, which have distinct angles that are not circular in shape, which in turn prevent rotation of the frame inside the housing. The guide ribs are also configured to interface with the trigger assembly guide rails 129 to allow axial movement and prevent rotation of the trigger assembly with respect to the housing. It should be noted that guide rails 129 interface with frame flange 144, which is used as backstop for the end of the stroke of the trigger assembly when extending, such as shown in FIG. 12T.

Figure 5A:
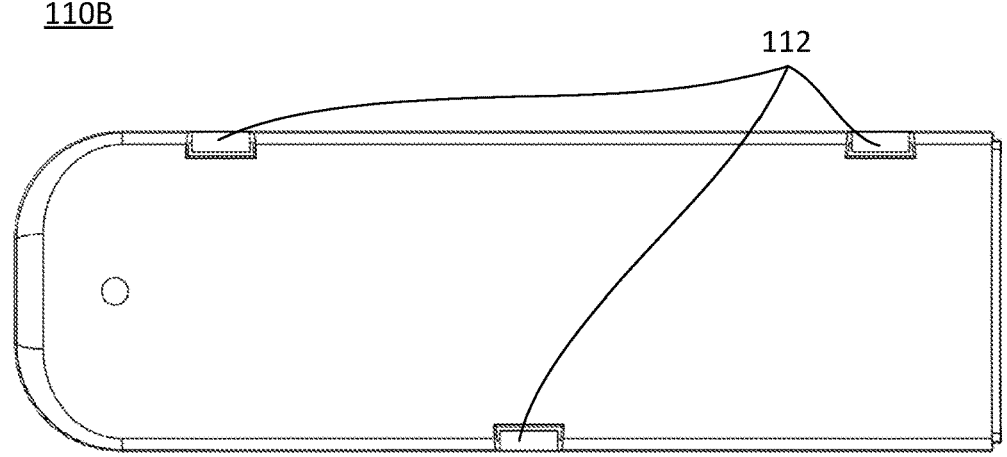
FIGS. 5A-E illustrate various views of the housing element 110B of the injector training device of FIG. 1A.
Figure 5B:
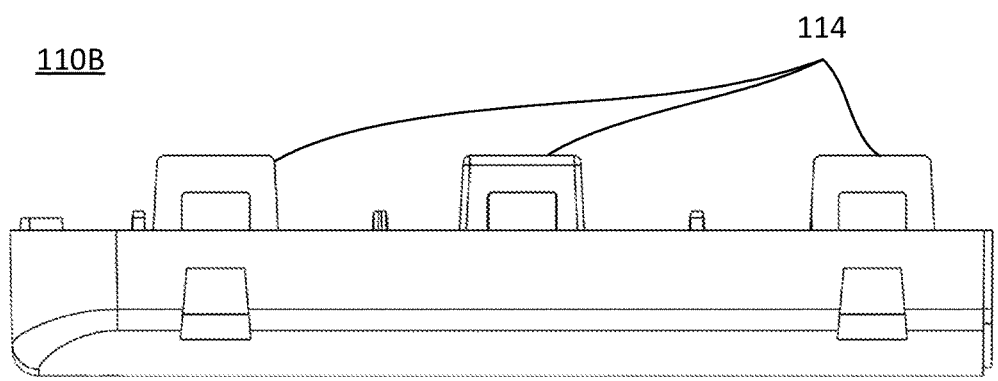
Figure 5C:
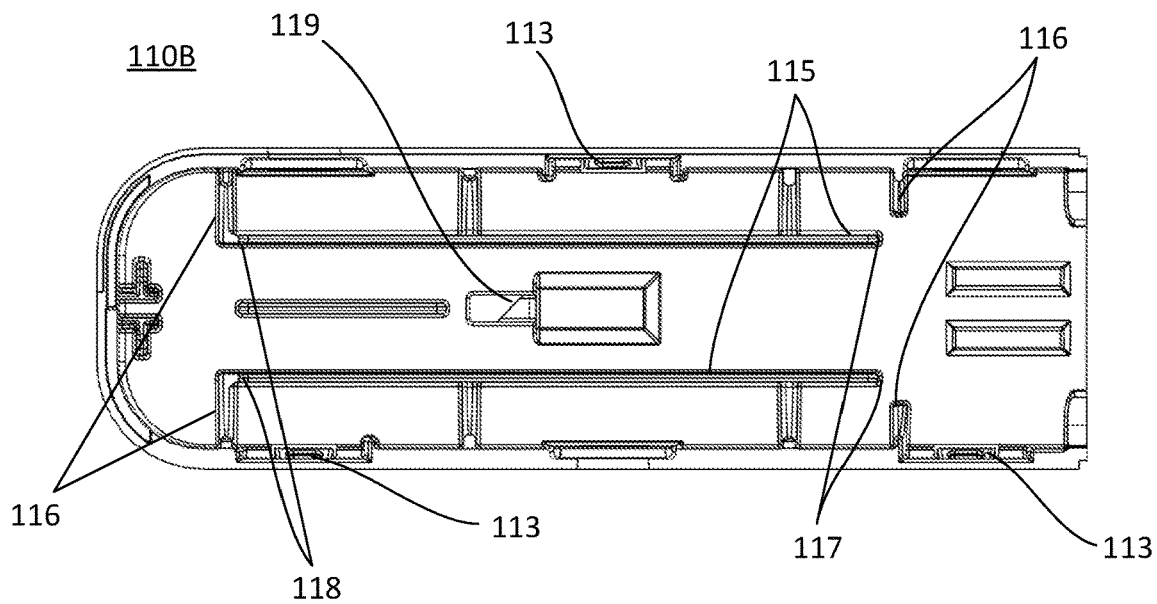
Figure 5D:
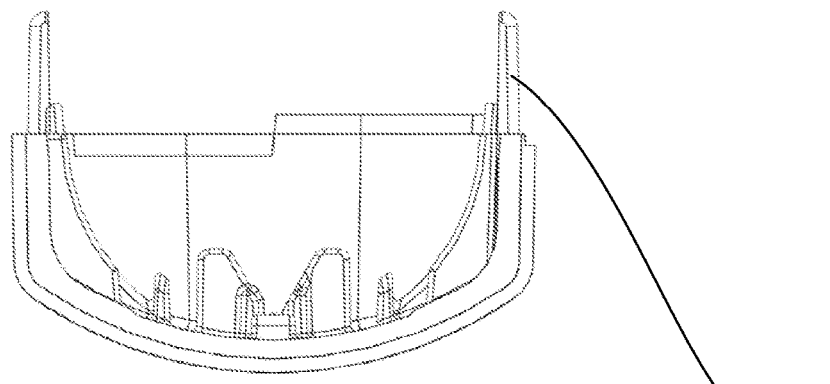
Figure 5E:
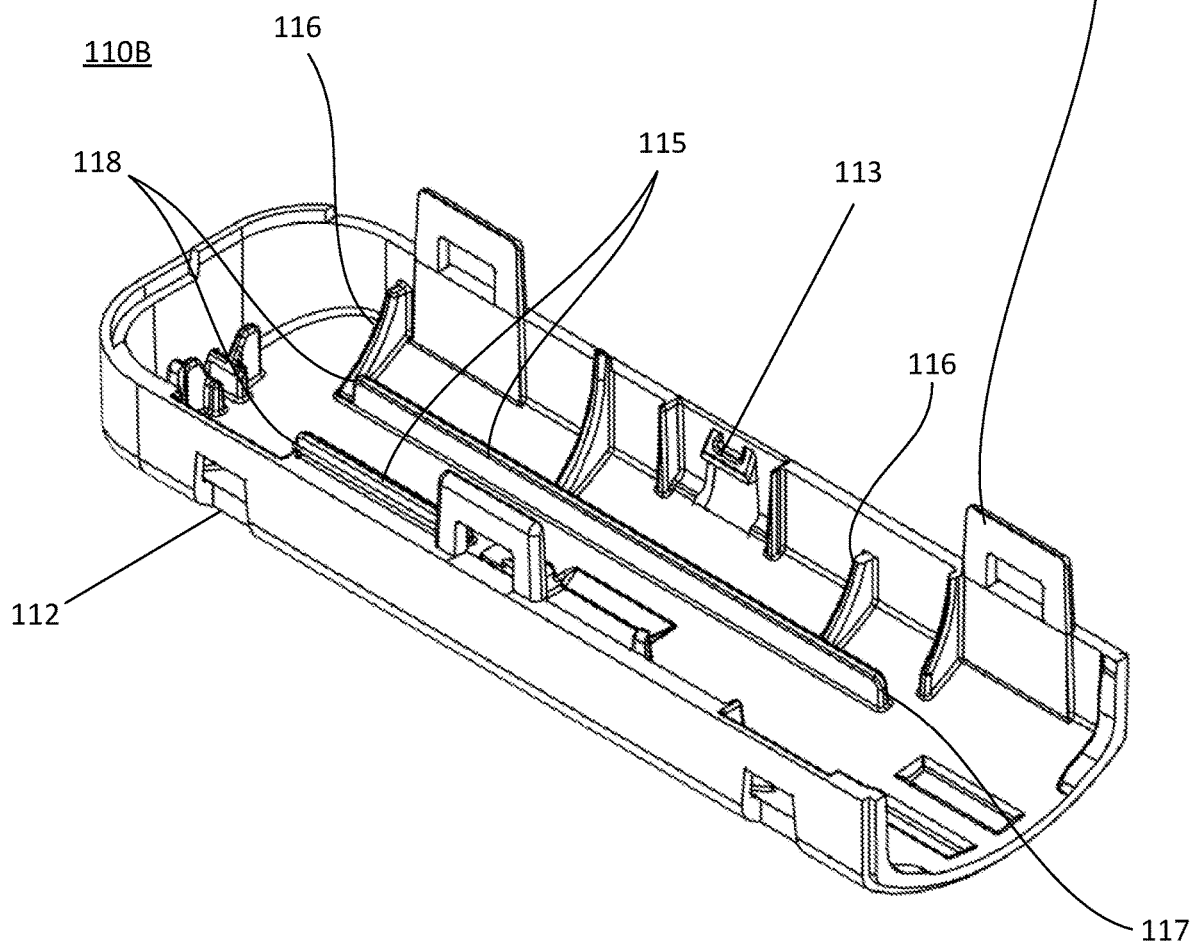

Another feature disposed on an interior sidewall of the housing component 110B is ramp feature 119. This feature is configured to interface with the two-way snap element 125 of the trigger assembly, which element 125 has the ability to flex in two directions. When interfacing with ramp feature 119 and traveling in a distal direction the two-way snap element is directed into a first plane as a result of the angled ramp, as best shown in FIG. 5C of 119. Once the two-way snap passes by 119 it returns to its nominal position and upon doing so makes a clicking sound. When element 125 travels in a proximal direction, such as when trigger assembly 120 is being depressed (to mimic depressing a bump trigger) and activated, the two-way snap ramp 128 of 125 allows 125 to move in the direction of a second plane that is generally orthogonal to the first plane. Again, upon overcoming the ramp feature 119, element 125 makes another clicking sound.

Figure 6A:
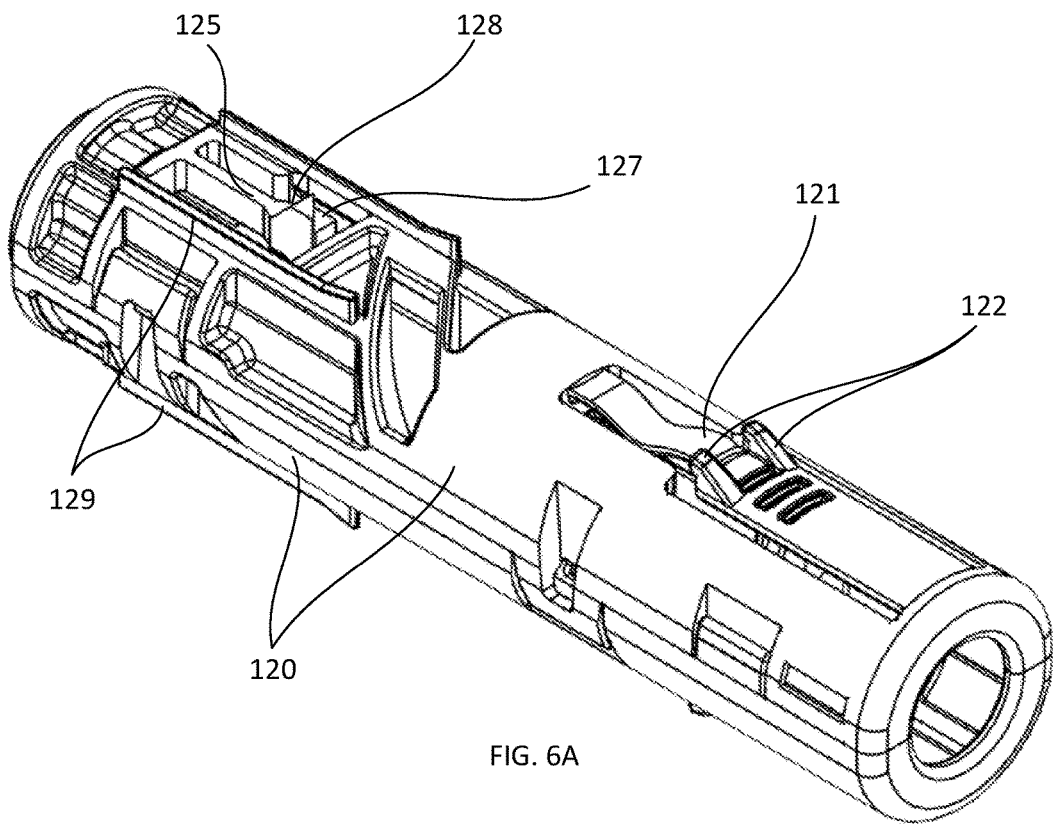
FIGS. 6A-B illustrate various views of the features of the trigger assembly in an assembled state.
Figure 6B:
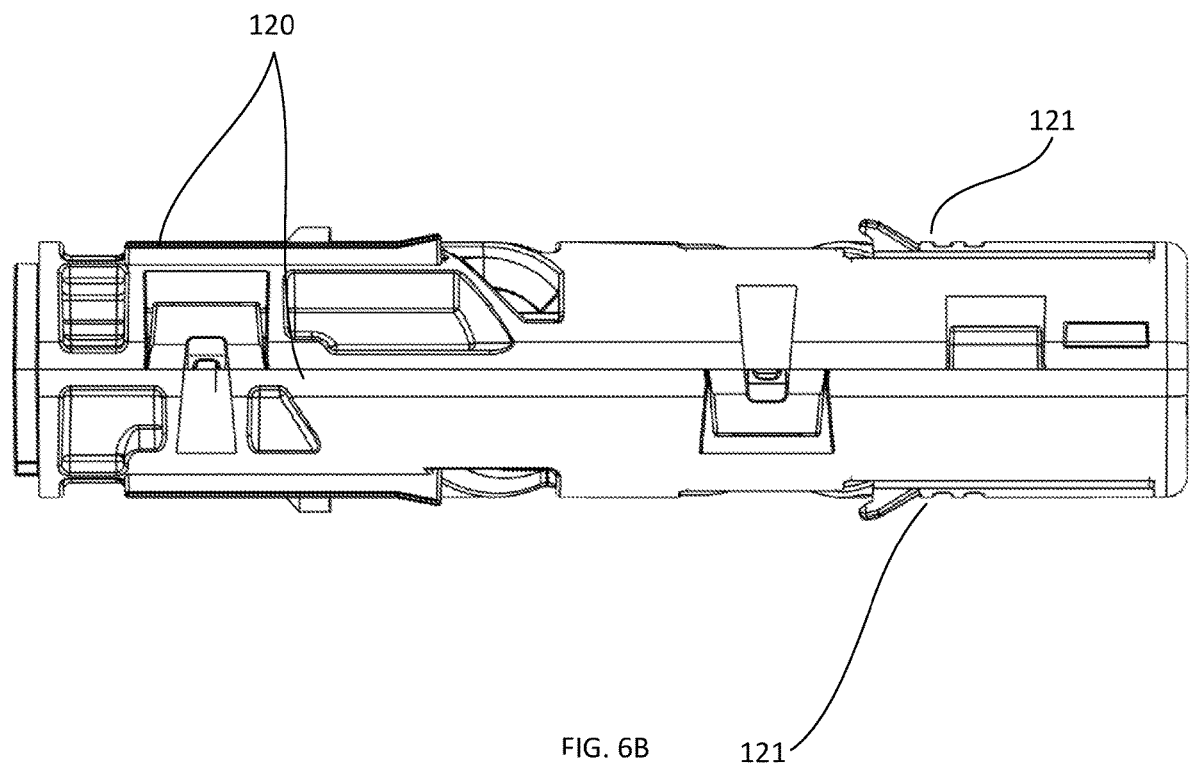
Figure 6C:
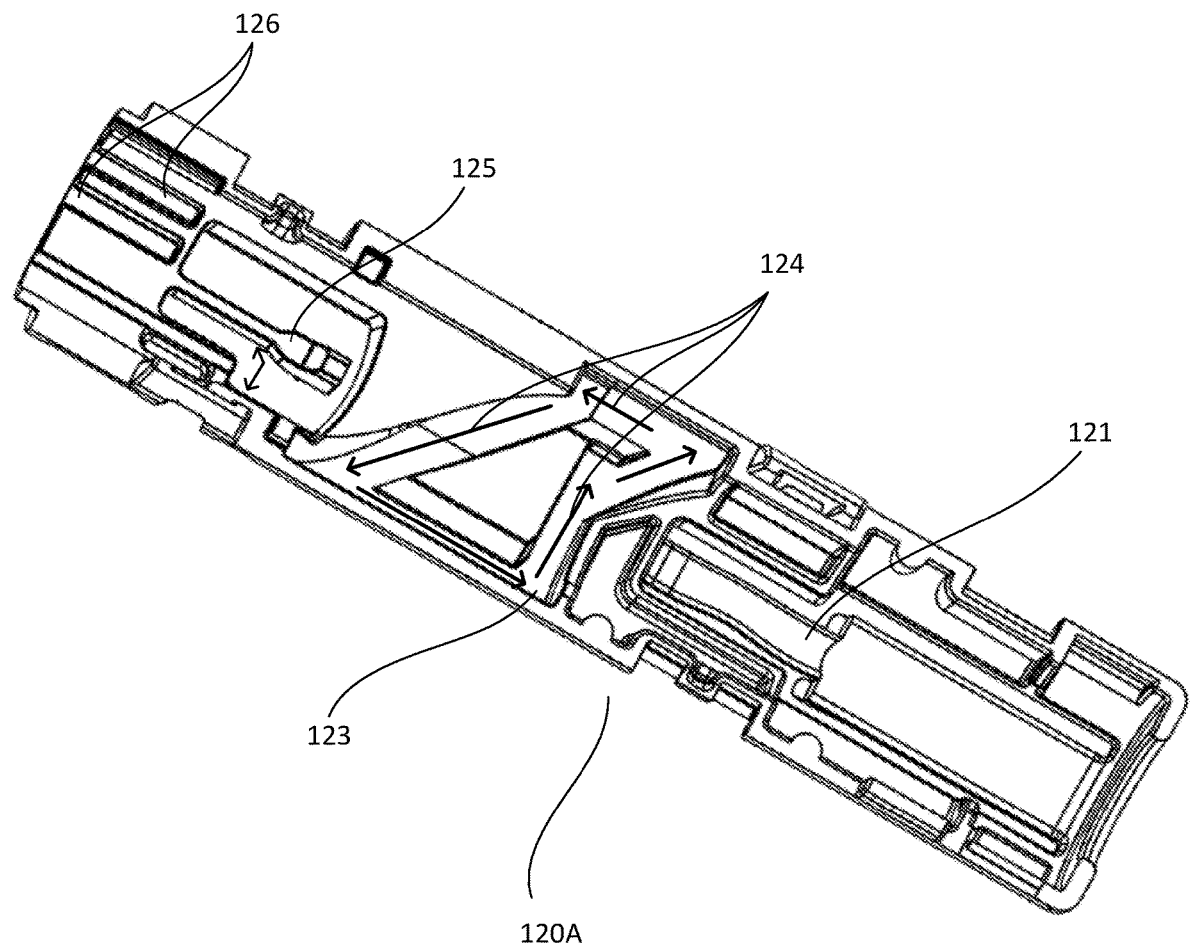
FIG. 6C illustrates an inside perspective view of the trigger assembly component 120A.

FIGS. 6A-6C illustrate various views of trigger assembly 120. Similar to housing 110, trigger assembly 120 is form of two trigger assembly components 120A and 120B. Also similar to housing components 110A-B, components 120A and 120B are made identical. This is not required, but has advantages as noted above. Components 120A an 120B also have tabs and attachment features that work similarly to those of the housing components 110A and 110B. These tabs and attachment features are shown, but not labeled, as one skilled in the art can see from the drawings how these are formed, especially when compared with 110A.

Some of the more active features of trigger assembly 120 include the trigger assembly lockout snap system 121 with lockout snap protrusions 122. This system 121 is configured flex and upon traveling in the distal direction can utilize the lockout snap protrusions to fix the trigger assembly in place and prevent movement once extended. FIG. 12.S.1-3 illustrate the travel path and flexing of lockout snap system 121 and where the snap protrusions 122 interface with the frame 140. The snap protrusions 122 when the trigger assembly are not in an extended state are disposed within frame aperture 148 of frame 140.

Figure 12B:
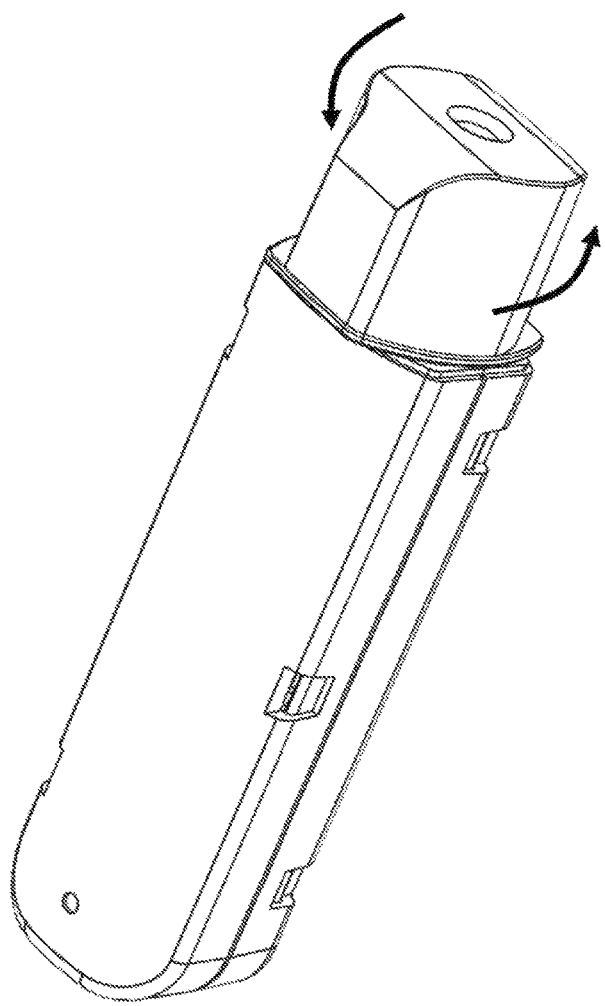
FIGS. 12A-GG provide illustrations of each of the various steps of the diagram of FIGS. 11A-E.
Figure 12H:
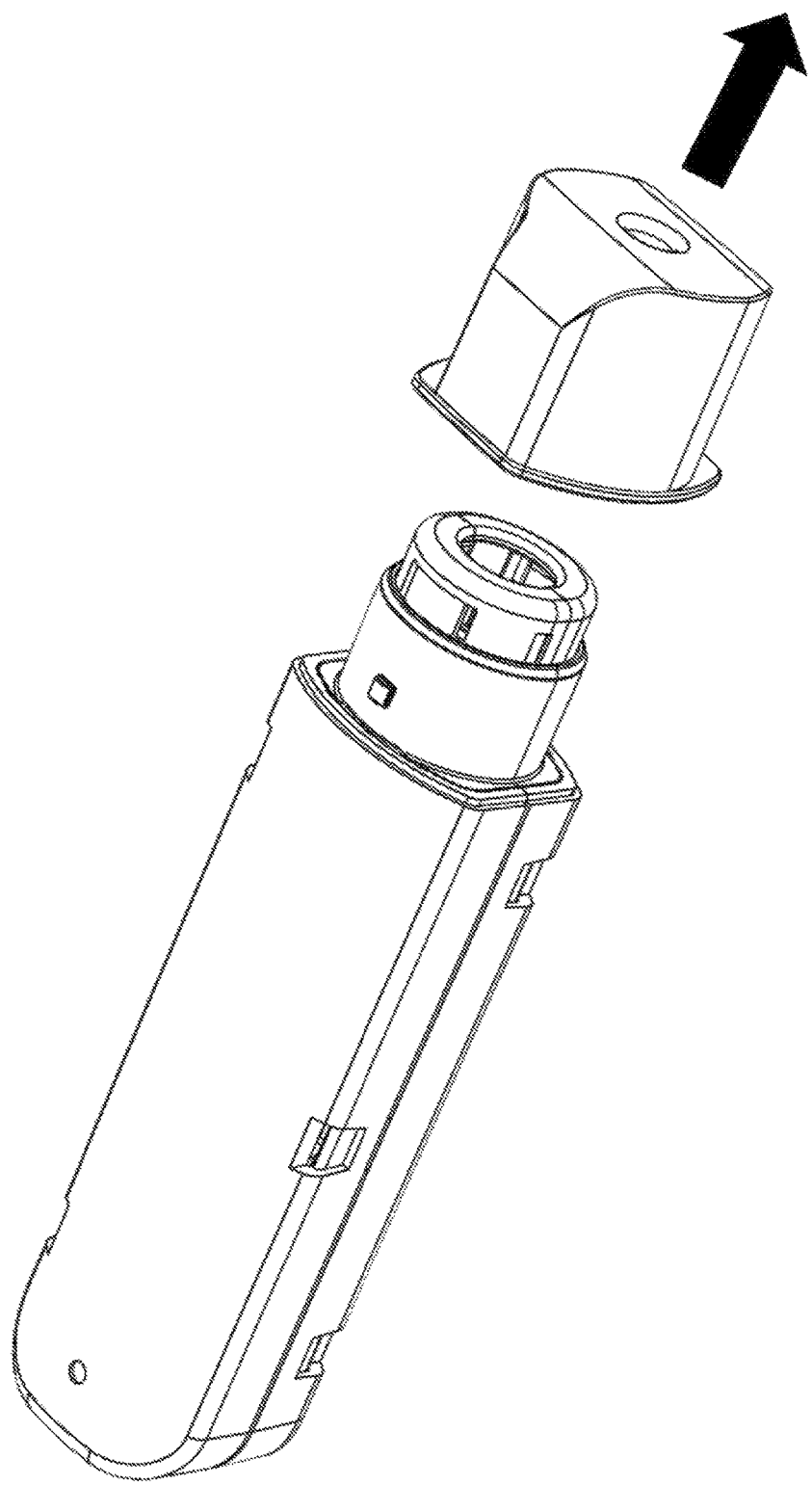
Figure 12I:
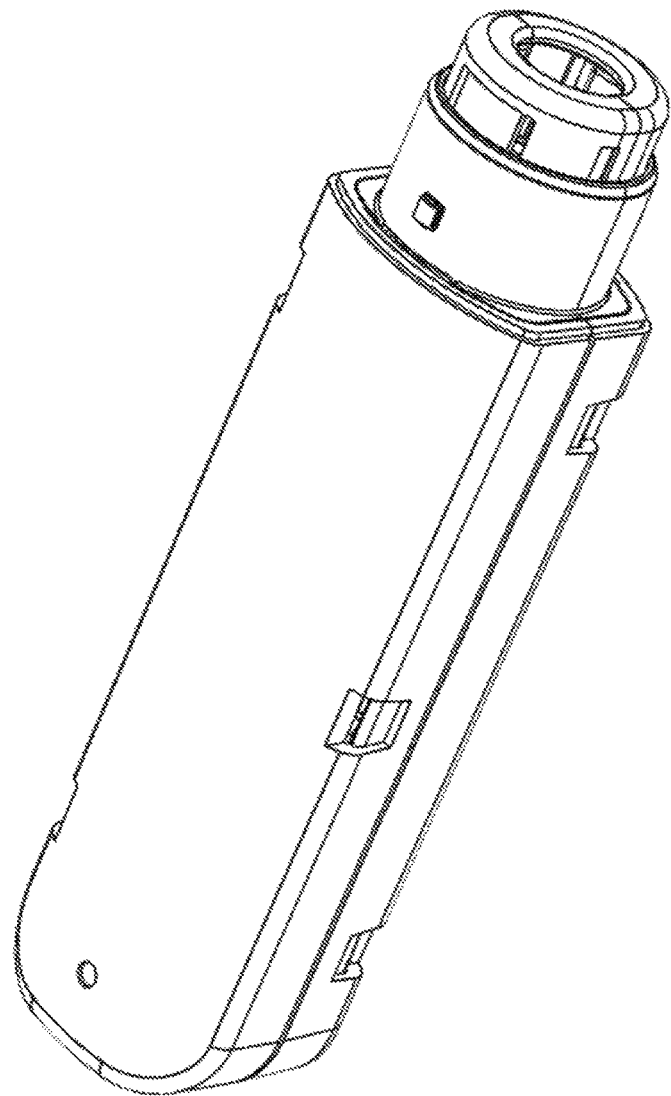
Figure 12J:
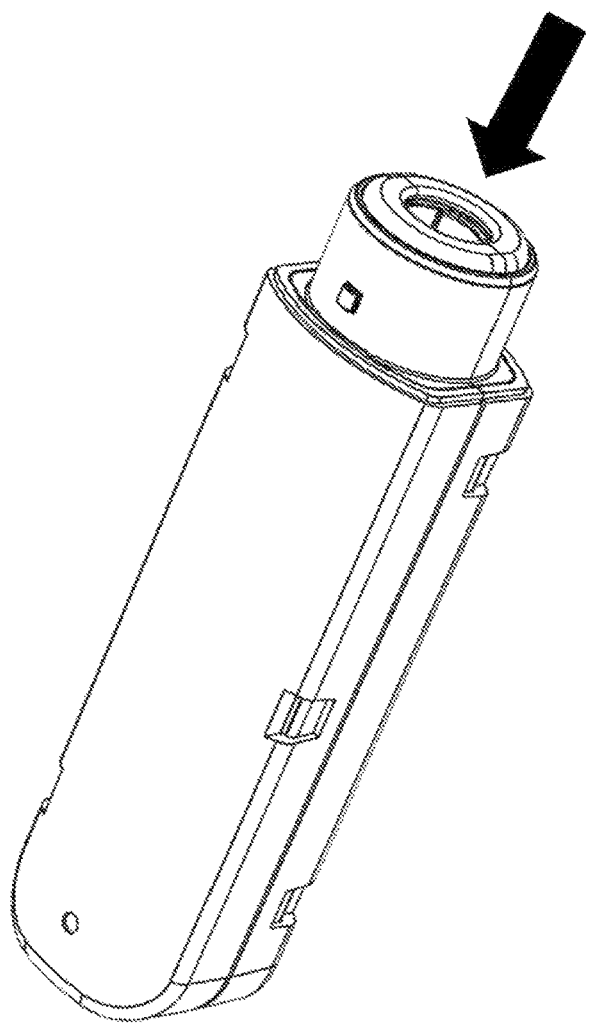
Figure 12M:
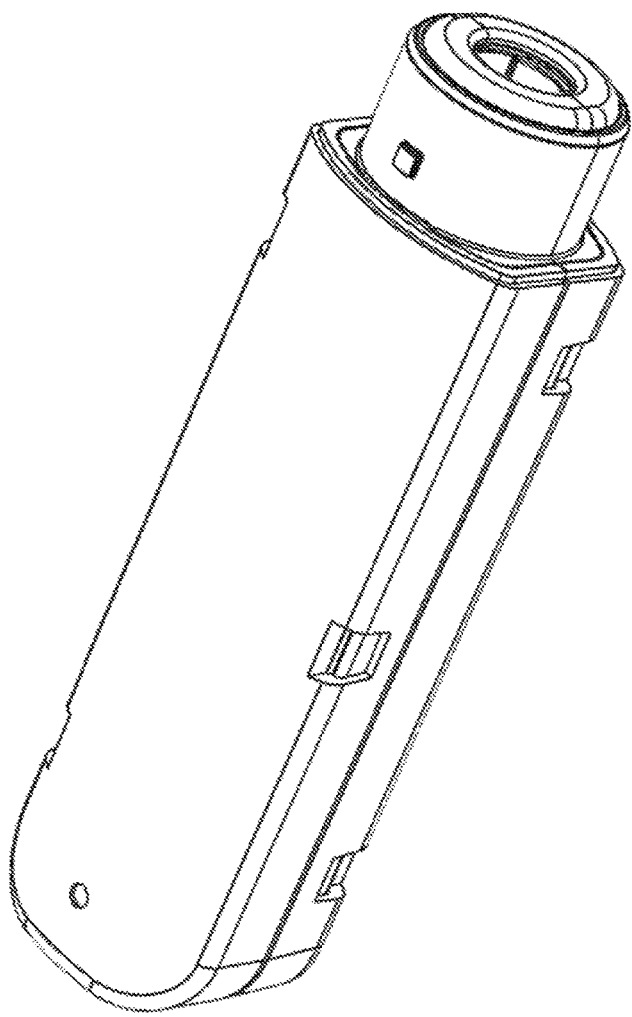
Figure 12N:
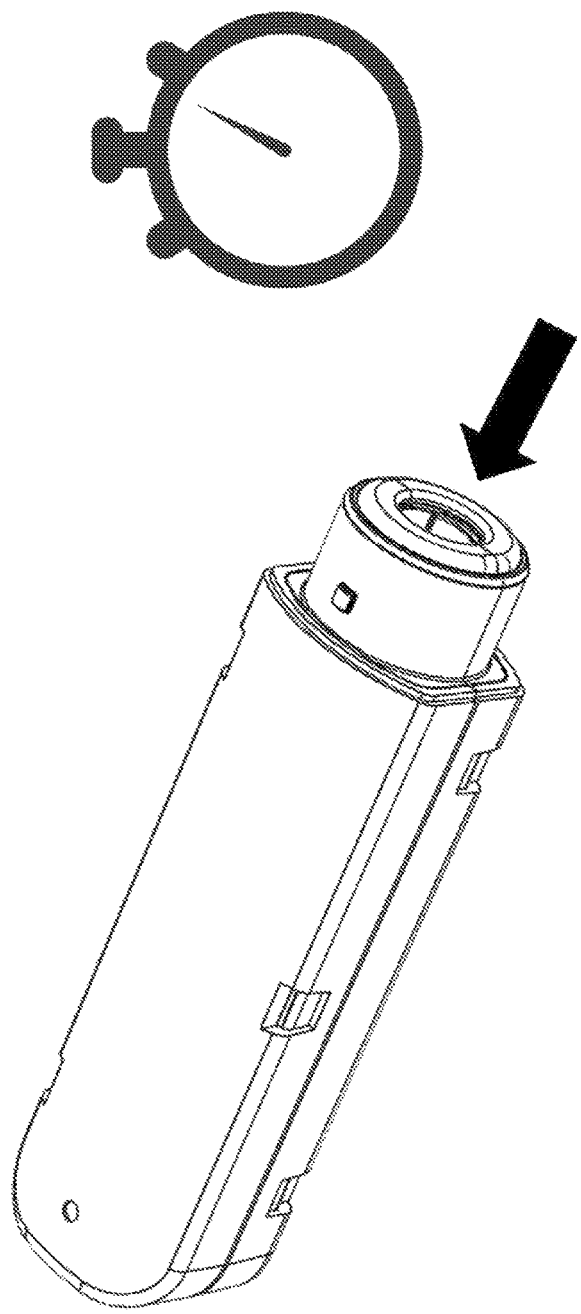
Figure 120:
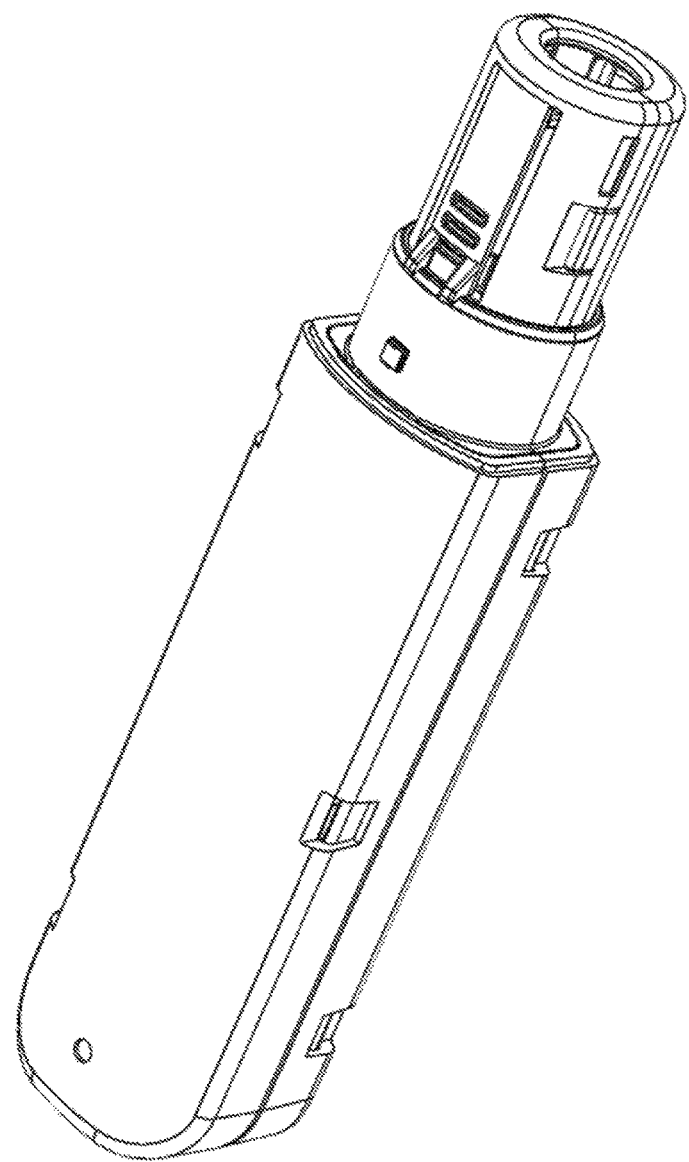
Figure 12U:
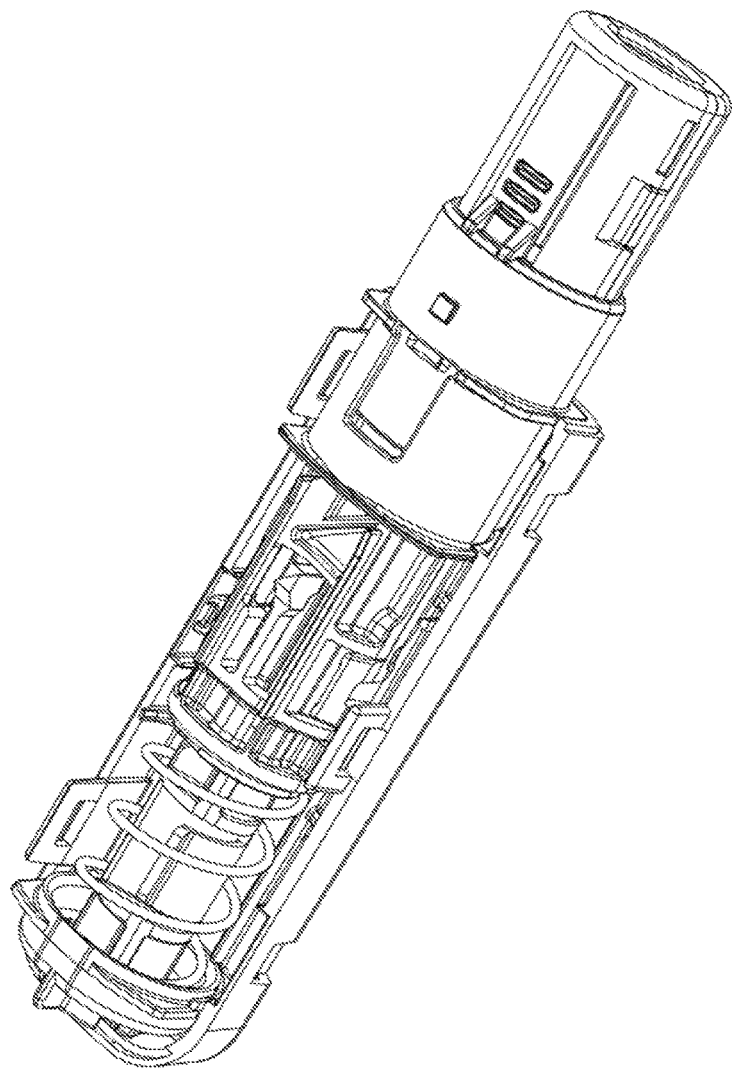
Figure 12V:
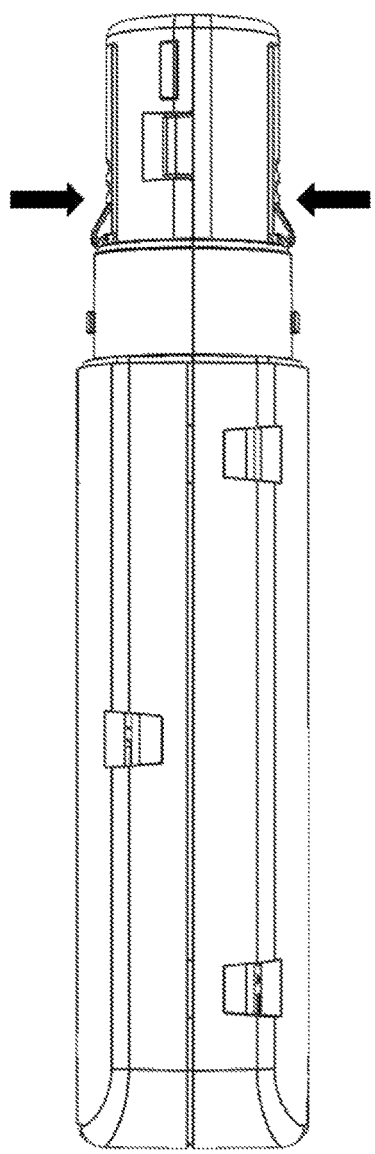
Figure 12W:
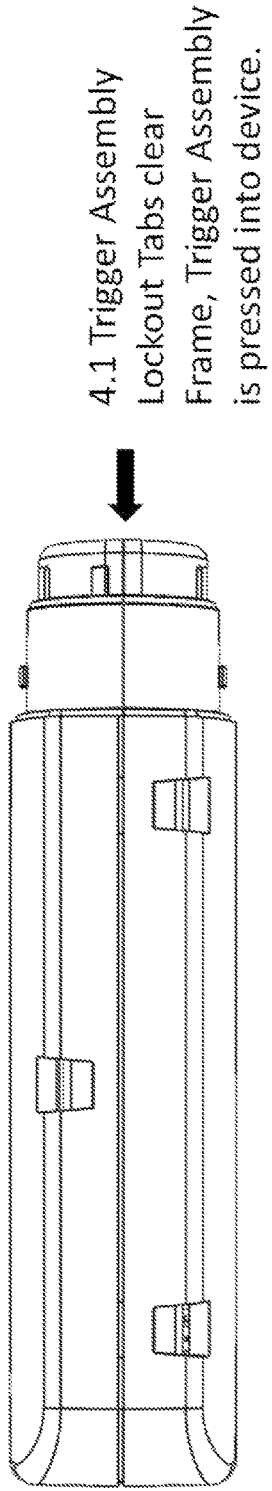
Figure 12Y:
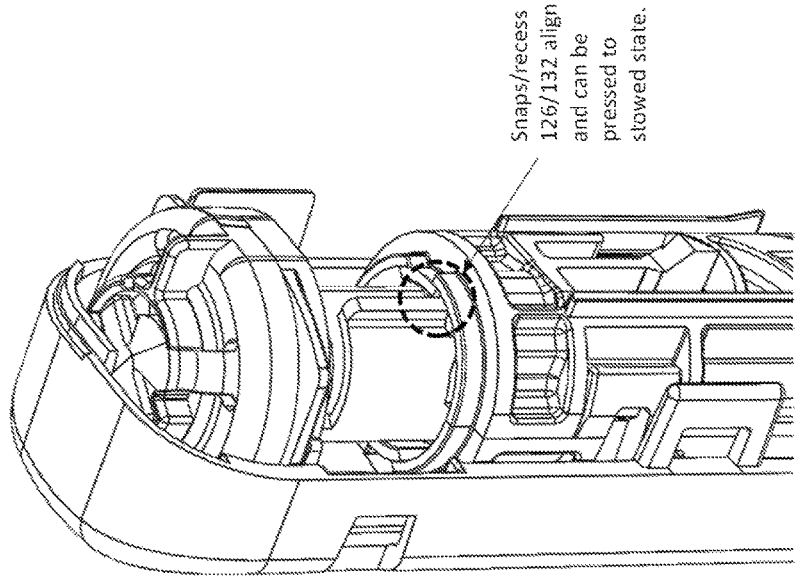

It should be noted that the trigger assembly is meant to mimic both the bump trigger of an injector and/or autoinjector mixing and delivery device as well as well as the needle shield. The purpose of the needle shield is to cover the needle after it has been used during the operation of the autoinjector device to prevent further harm to others handling the activated autoinjector. The needle shield covers the needle and has lockout features that prevent it from being depressed again, thus minimizing harm. However, as this device is meant for training and repeatability, the lockout snap system 121 can be reset by pinching or flexing the lockout snap system 121, so the snap protrusions 122 can flex inward and the trigger assembly again be depressed or inserted into the housing 110 pass the frame 140, as shown in FIGS. 12V-X.

Figure 12A:
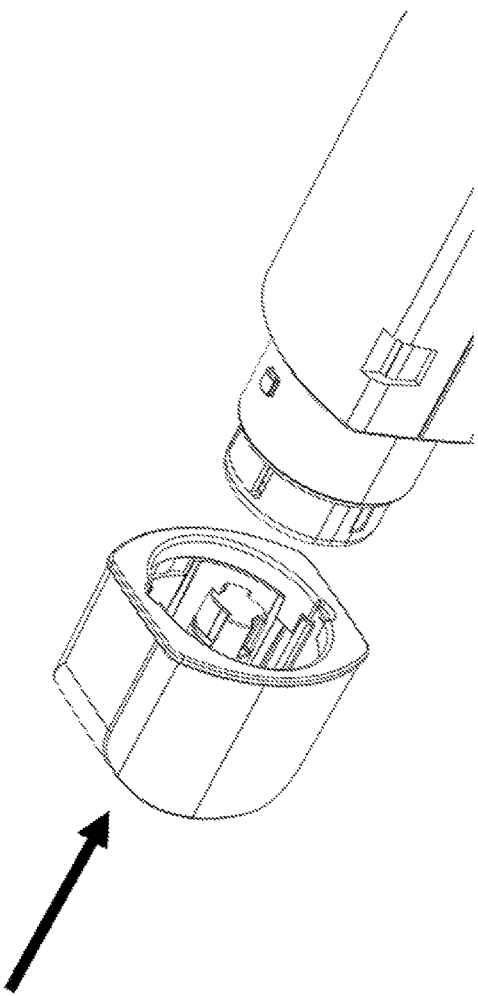
Figure 12B:
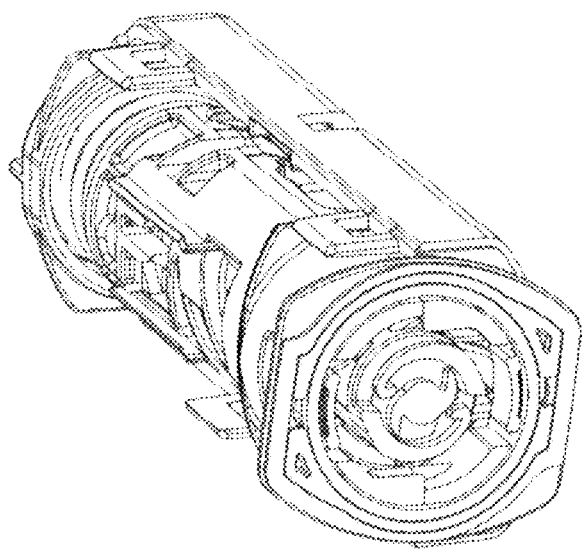
Figure 12C:
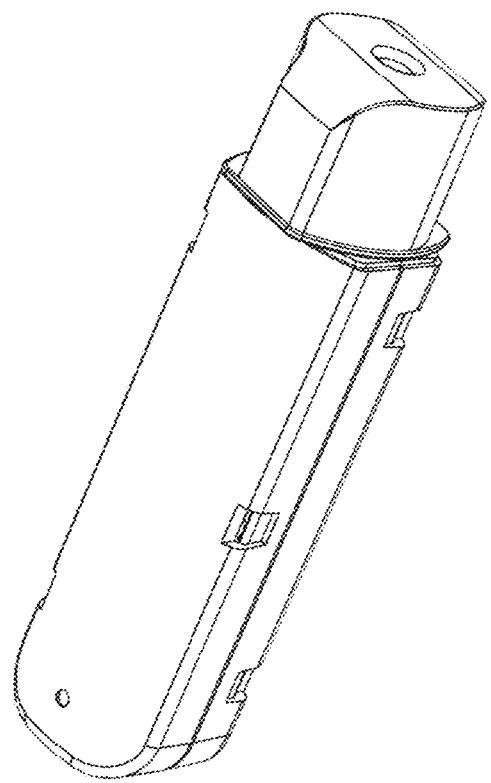
Figure 12E:
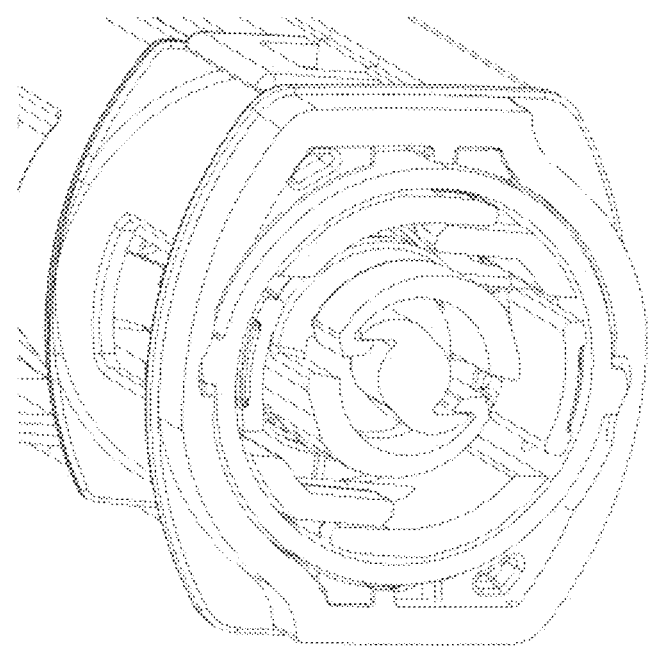
Figure 12F:
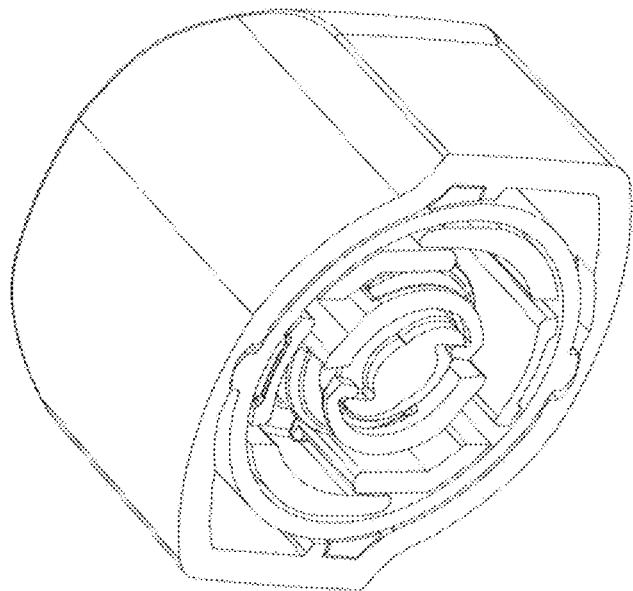
Figure 12G:
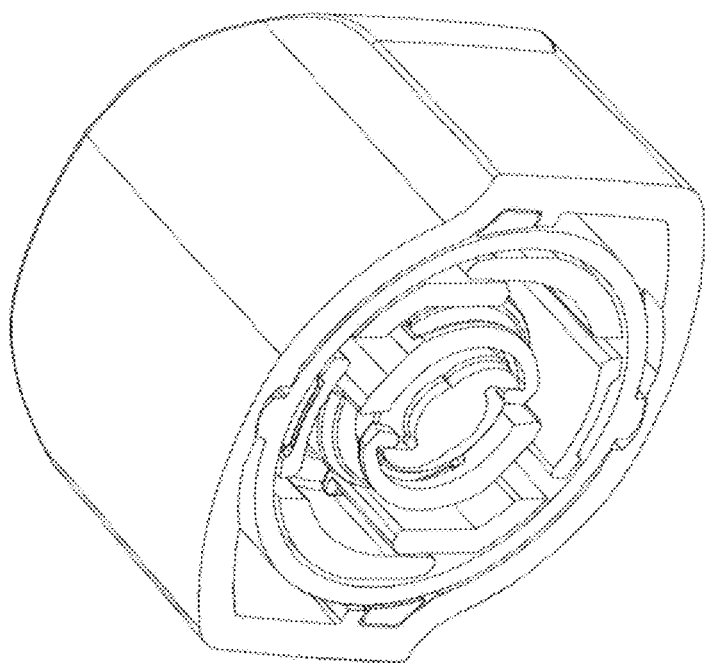

The two-way snap element 125 as mentioned above interfaces with 119 and is primarily used to provide appropriate clicking sounds indicative of those during the various activation states of a real autoinjector device, such as illustrated in FIGS. 12K.1-4 and 12R.1-4. The two-way snap element 125 also interfaces with some of the ribs of drum 130 to prevent axial translation at certain times, as shown in FIGS. 12G.1-3. As noted above the two-way snap element 125 has a two-way snap angled edge 127 and a two-way snap ramp 128 feature that interface with housing ramp feature 119 in two different planes as noted above.

FIG. 6C illustrates the interior portion of trigger assembly component 120A, which shows the drum protrusion channels 123, which forms the drum protrusion pathway 124. FIG. 6C also illustrates with arrows the directions in the two planes two-way snap element 125 can move, as well as trigger assembly snap recesses 126.

Figure 6D:
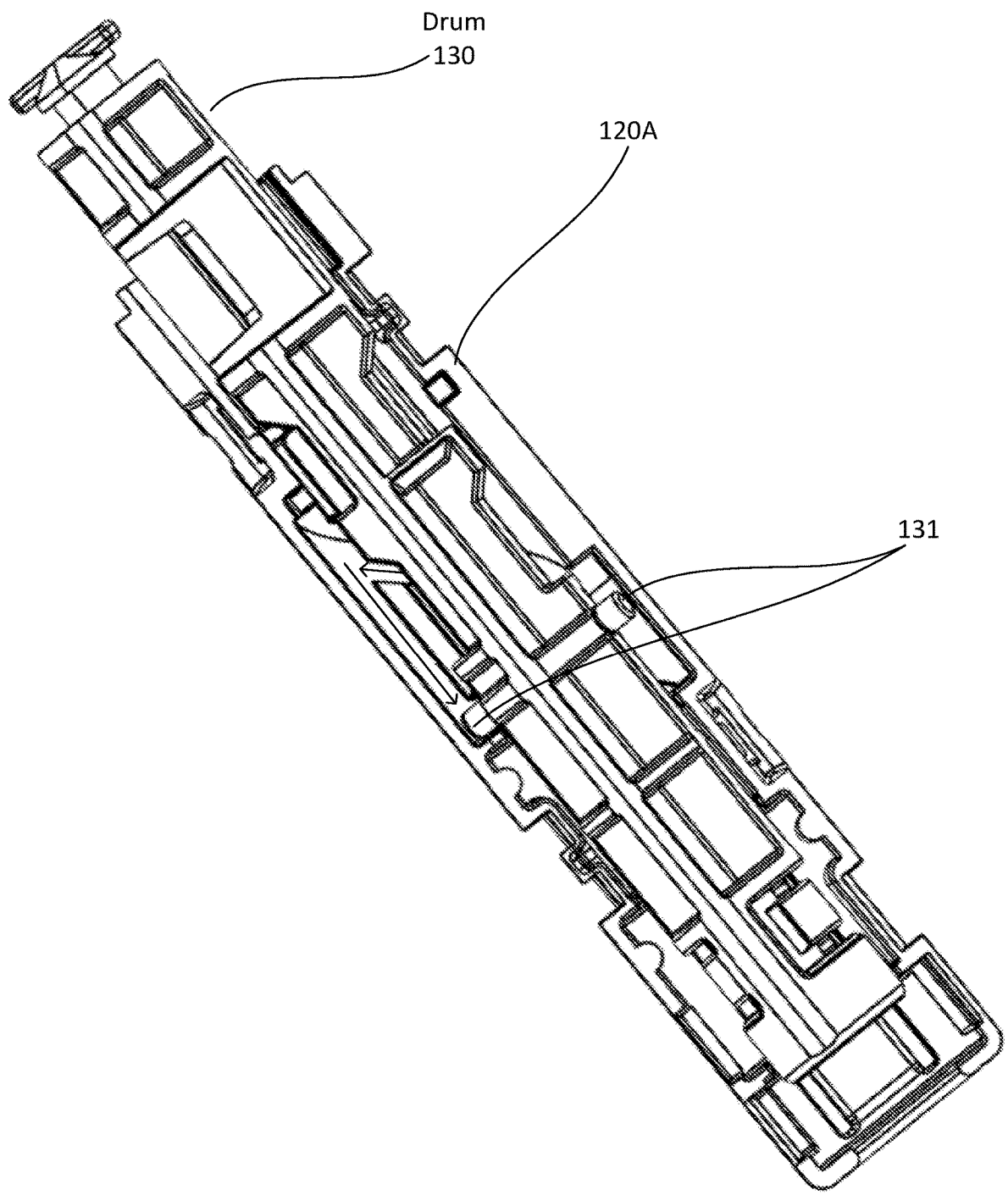
FIG. 6D illustrates an inside perspective view the trigger assembly component 120A having a drum assembly 130 situated therein.
Figure 7A:
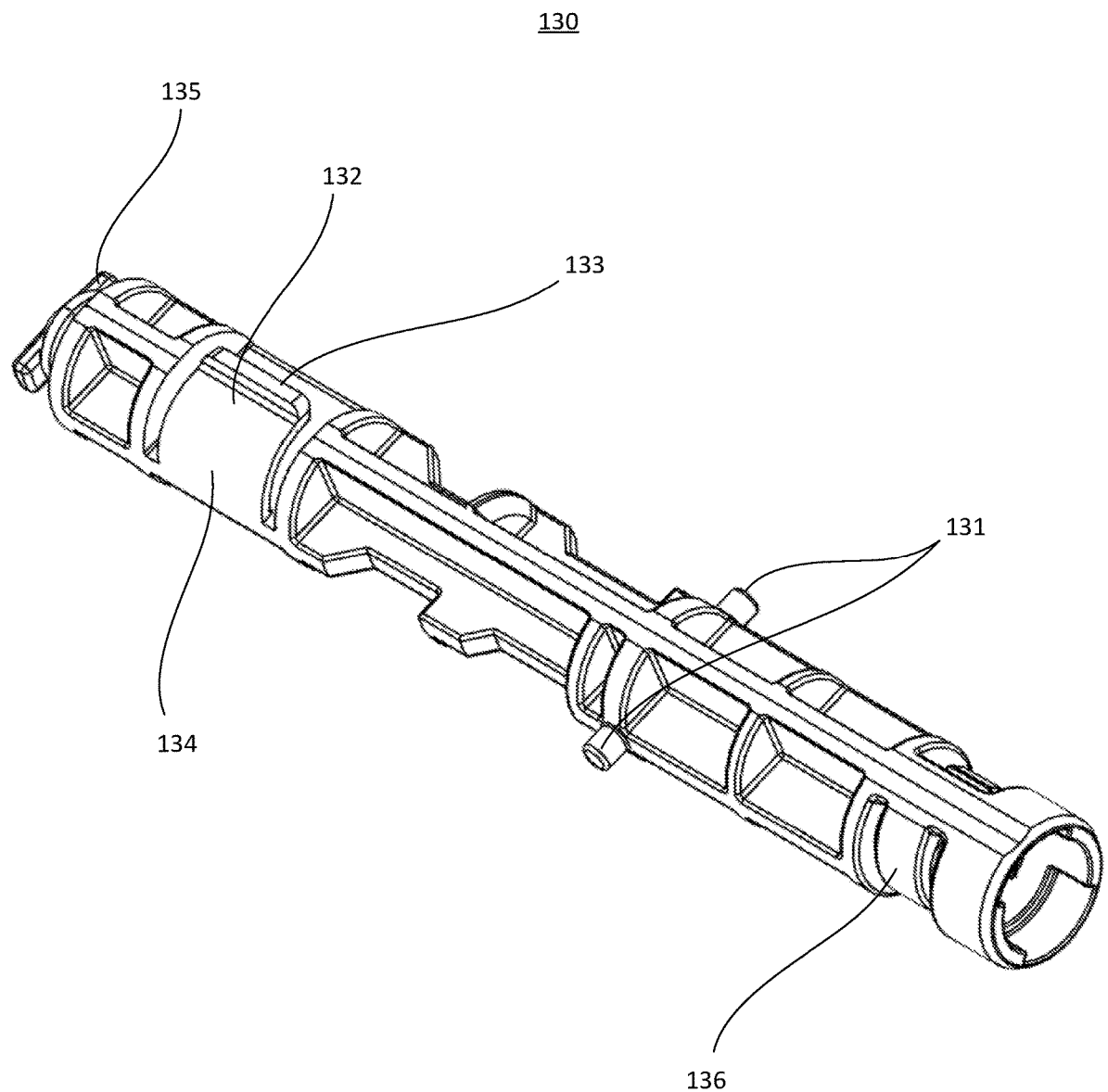
FIGS. 7A-E illustrate various views of the drum assembly of an injector training device.
Figure 7B:
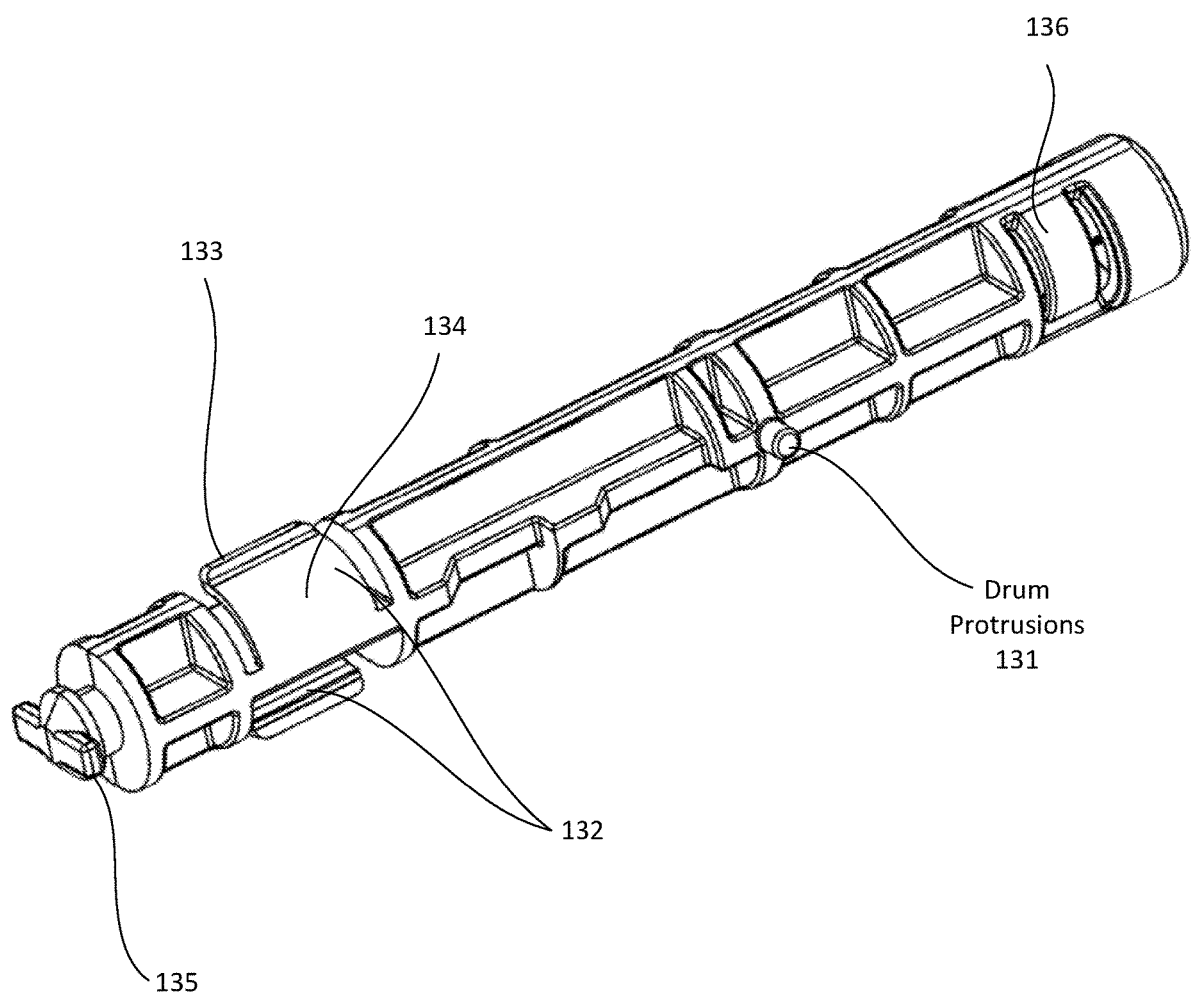
Figure 7C:
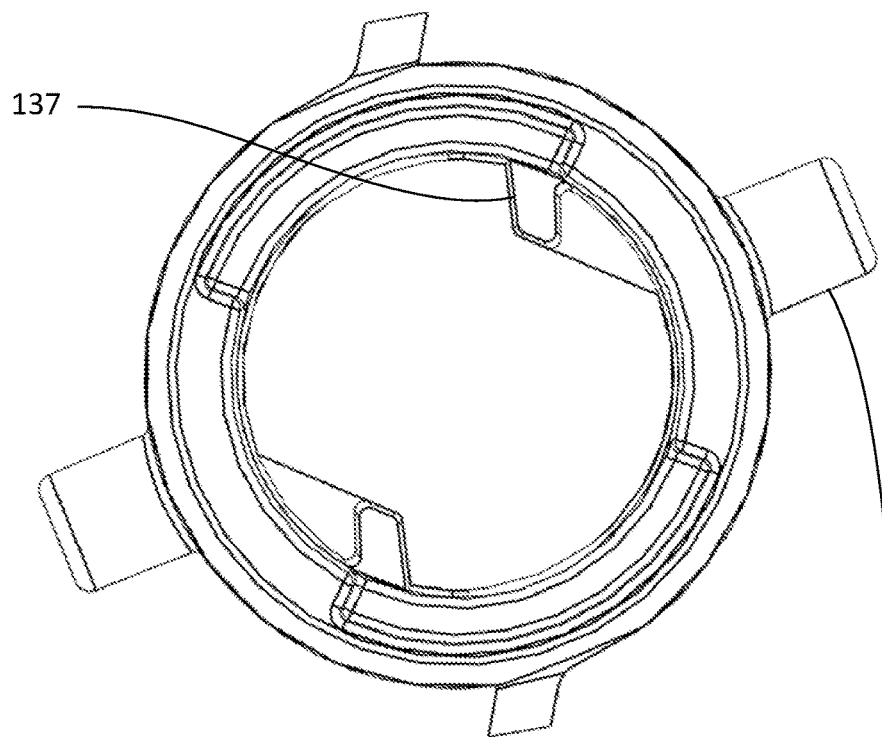
Figure 7D:
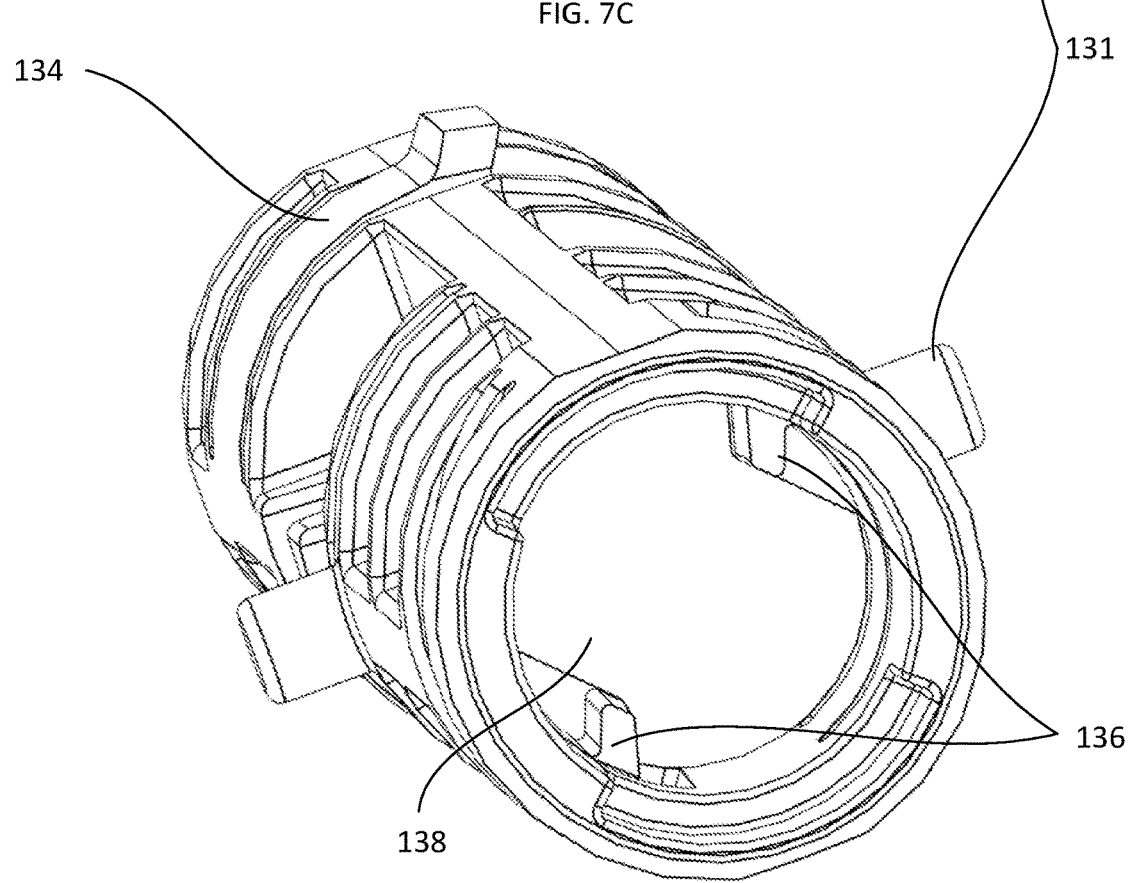
Figure 7E:
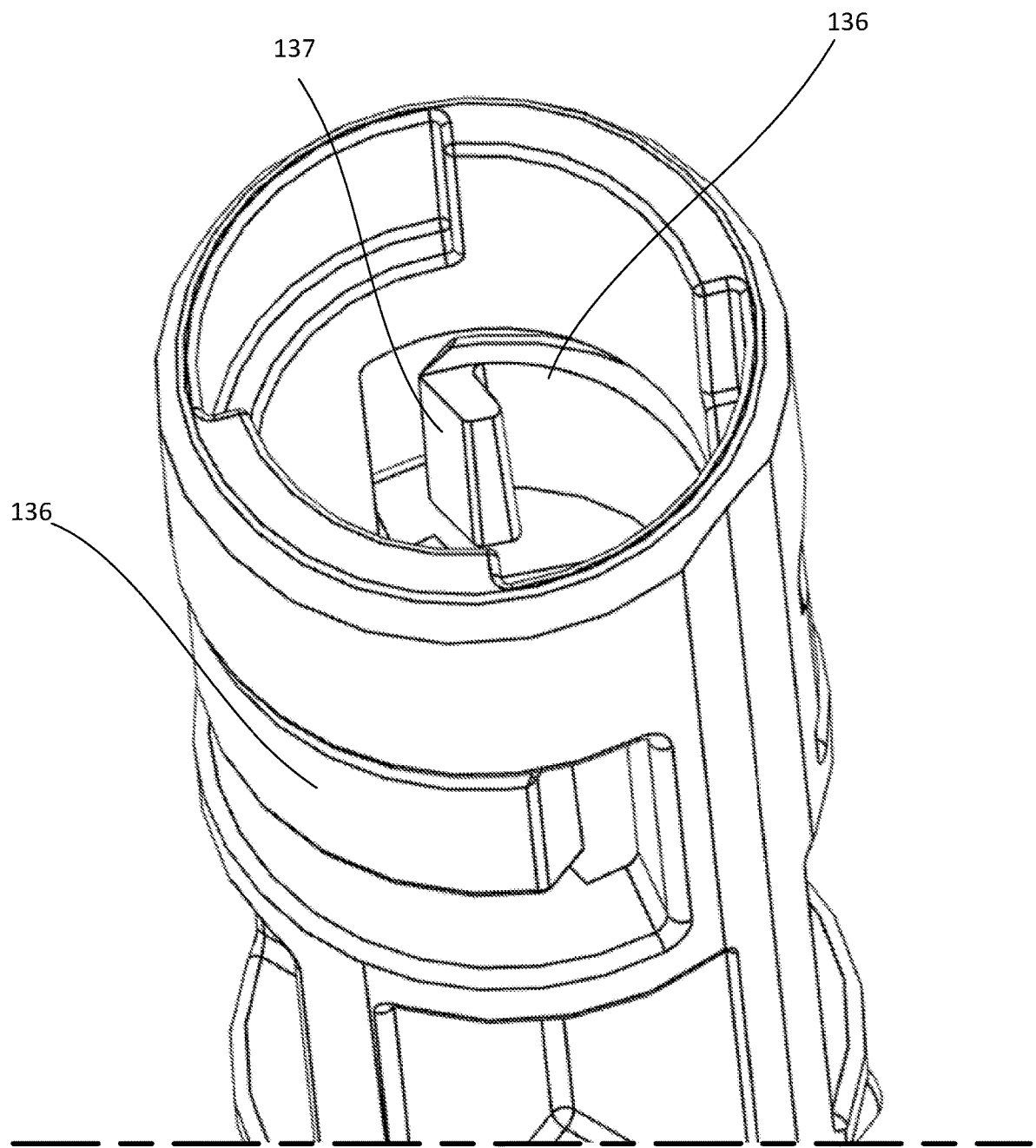

FIG. 6D illustrates drum 130 inserted into trigger assembly component 120A to show where drum protrusions 131 are to interface with the drum protrusion channels 123 of 120A. Other figures such as FIGS. 12D.1-4, 12L.1-4, and 12Q.1-5 illustrate drum protrusions 131 travel along drum protrusion pathway 124 at various steps in the process of using the injector training device 100. As shown, the drum protrusions 131 within channels 123, allow the drum 130 to travel in a rotational manner depending on the direction of the channels 123 within the pathway 124 with respect to the trigger assembly, but also allow the trigger assembly to travel axially with respect to drum assembly 130.

FIGS. 7A-E illustrate various views of the drum assembly 130 of the injector training device 100. Already noted are drum protrusions 131 that each interface with the drum channels 123 formed on the interior sidewall of trigger assembly components 120A and 120B.

The drum assembly 130 is also configured to have two drum anti-rotation snaps 132 comprised of an anti-rotation snap tab feature 133 and an anti-rotation snap flex arm 134. The anti-rotation snaps serve at least purposes being to cause the drum assembly to only rotate in one direction and cause clicking or snapping sounds at the appropriate times when rotated, as part of the attempt to mimic the real-life clicking sounds of a real autoinjector device. The anti-rotation snaps 132 interface with the trigger assembly snap recesses 126 of 120A and 120B. FIGS. 12E.1-5 illustrate the interaction between 132 and recesses 126 in various positions and when the clicking sound occurs when the drum assembly 130 is rotated with respect to the trigger assembly 120. The tab 133 interfaces directly with the recess 126, while the flex arm 134 allows enough flexing to transfer from one position to the next all while rotating in only one direction. This rotating in only one-direction only applies when 132 is interfacing with 126. When the trigger assembly is in an extending state, the recesses 126 and anti-rotation snaps 132 are not engaged. For example, FIG. 6D shows them in an engaged state and FIG. 12U shows them in a disengaged state where trigger assembly 120 is extended.

The drum t-connector 135 is configured to engage the spring retainer 150 in a rotational manner, while fixing the drum in an axial translating manner. The t-connector has a t-shape when viewing from a side angle that allows it to initially pass into the retainer cross aperture 151 of spring retainer 150. Below the t-shape when viewing from side is an angled ramp or from a perspective view, has a conical shape leading up to the t portion and a circular base on the bottom portion. The ramp allows t-connector 135 to be pressed through the aperture 151 and then retained by the circular base. The t-portion is allowed to rotate within the retainer guide 155 until it abuts against retainer stop 157, which prevents further rotation. Thus, the t-connector can rotate in one-direction such as greater than 1 degree of rotation and less than 360 degrees of rotation and back in a second rotation again greater than 1 degree of rotation and less than 360 degrees of rotation. In a preferred embodiment the rotation amount is greater than 90 degrees and less than 180 degrees. The retainer spring 150 features are shown in FIGS. 9A-D. Similar to the frame 140, the spring retainer 150 has a retainer flange 153 that interfaces with and conforms in shape to the inner sidewalls of the housing components 110A and 110B, thus in similar manner prevent rotation of the spring retainer within 110. The spring retainer is also axially fixed within the housing 110 by cross ribs 116 located at the proximal end of the housing.

Figures 10A, 10B:
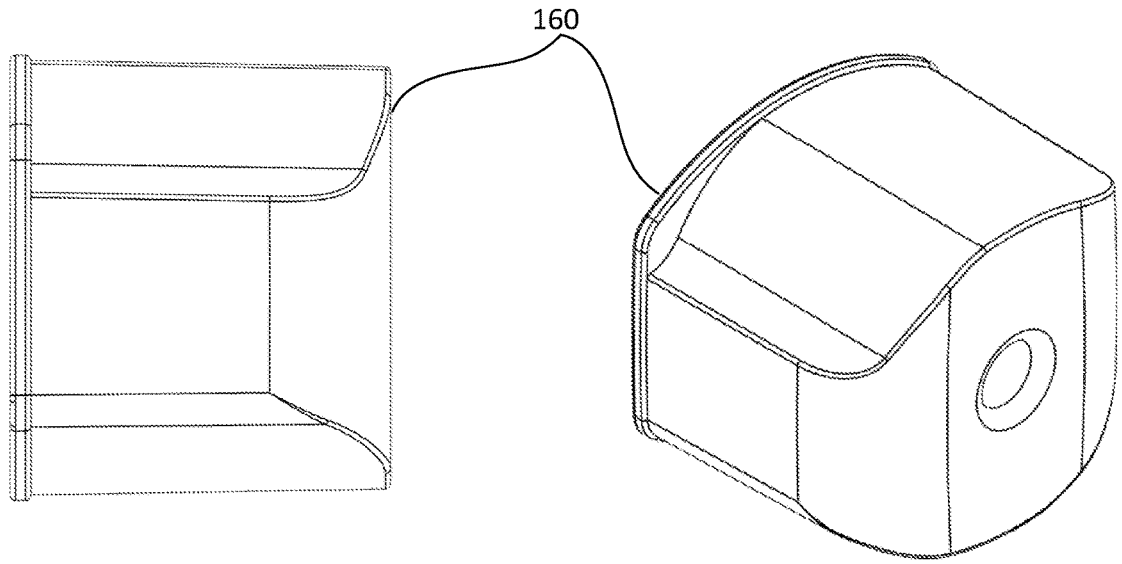
FIGS. 10A-D illustrate various views of a cap of an injector training device.
Figures 10C, 10D:
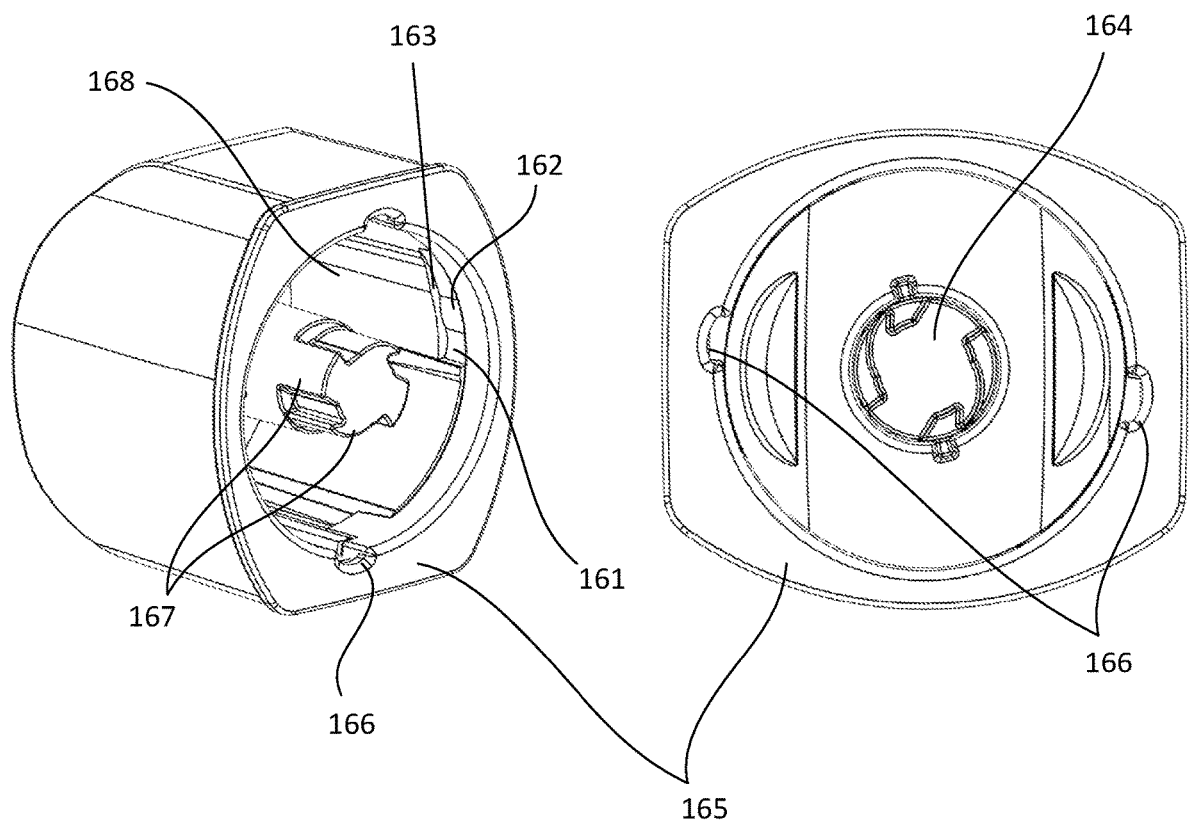

On the other end of the drum assembly 130 opposite of the t-connector 135 are the drum reset snap elements 136 with a reset snap angled protrusion 137 that protrudes inwardly into the upper drum cavity 138. The reset snap 136 is configured to interface with the spline 164 having spline elements 167 of the cap 160. The spline elements as shown in FIGS. 10C-D are angled to interface with the angle protrusion in a manner that allows the spline elements 167 to pass over (or rather push outward 136) when rotating in one direction, but then engaging 136 when rotating in the opposite direction, such that it causes the drum to rotate within the trigger assembly, when other features are not preventing rotation in a particular state, such as 132. The spline is configured to enter into the upper drum cavity to engage 136 and be removed from the upper drum cavity in certain states and when free from the frame protrusions 142.

Figure 8A:
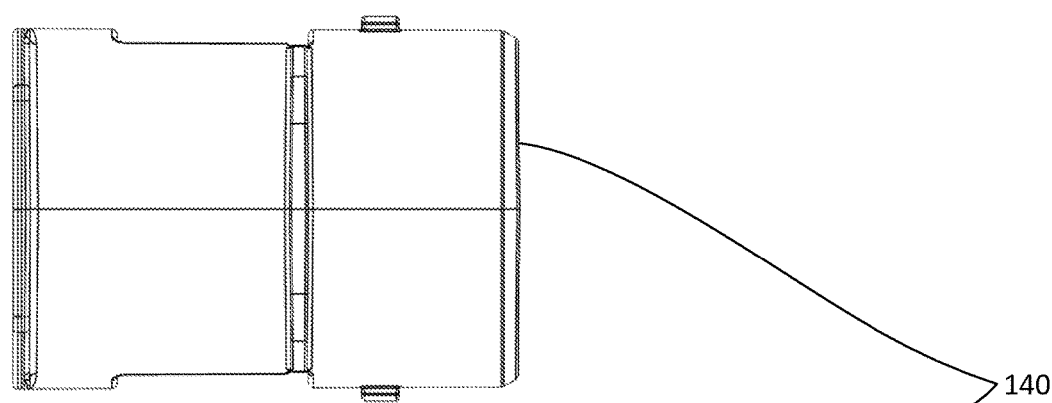
FIGS. 8A-C illustrate various views of a frame of an injector training device, including a cross-sectional perspective view FIG. 8B.
Figure 8C:
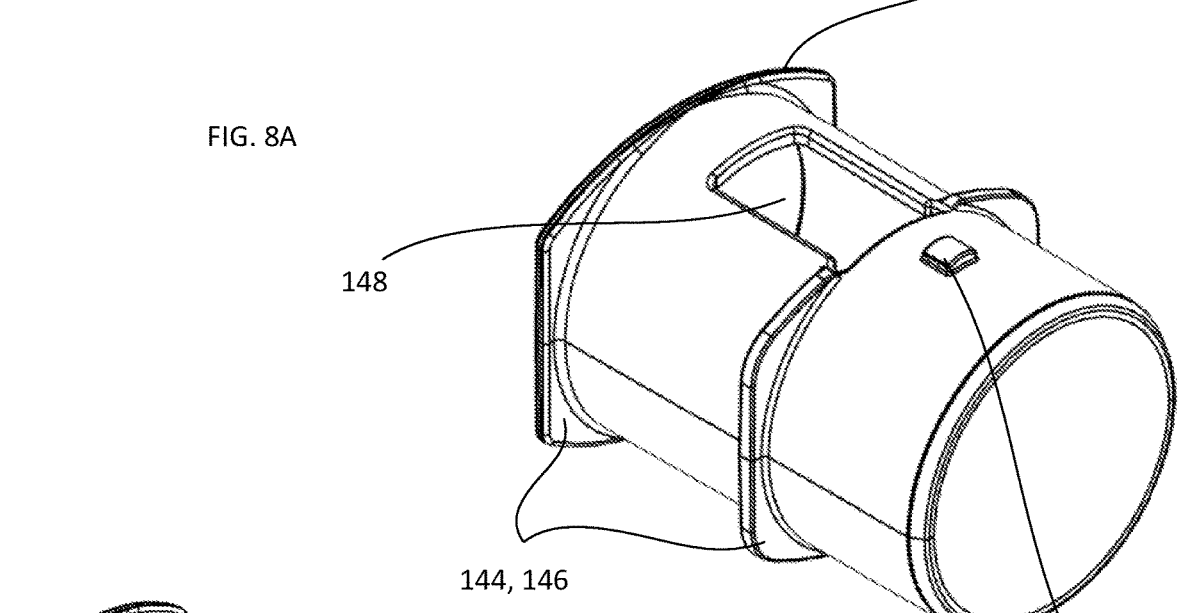
Figure 8B:
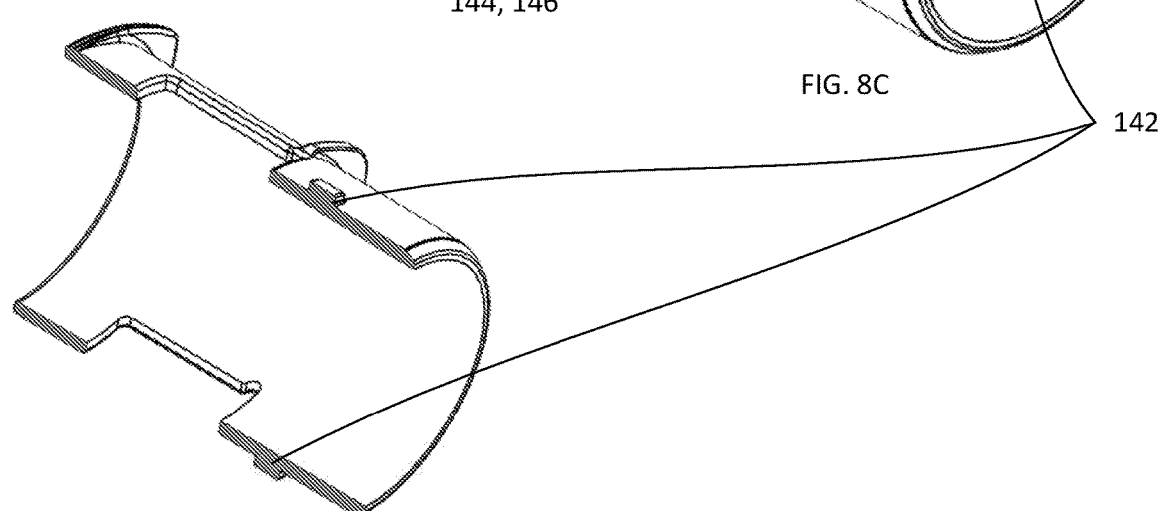
Figure 9A:
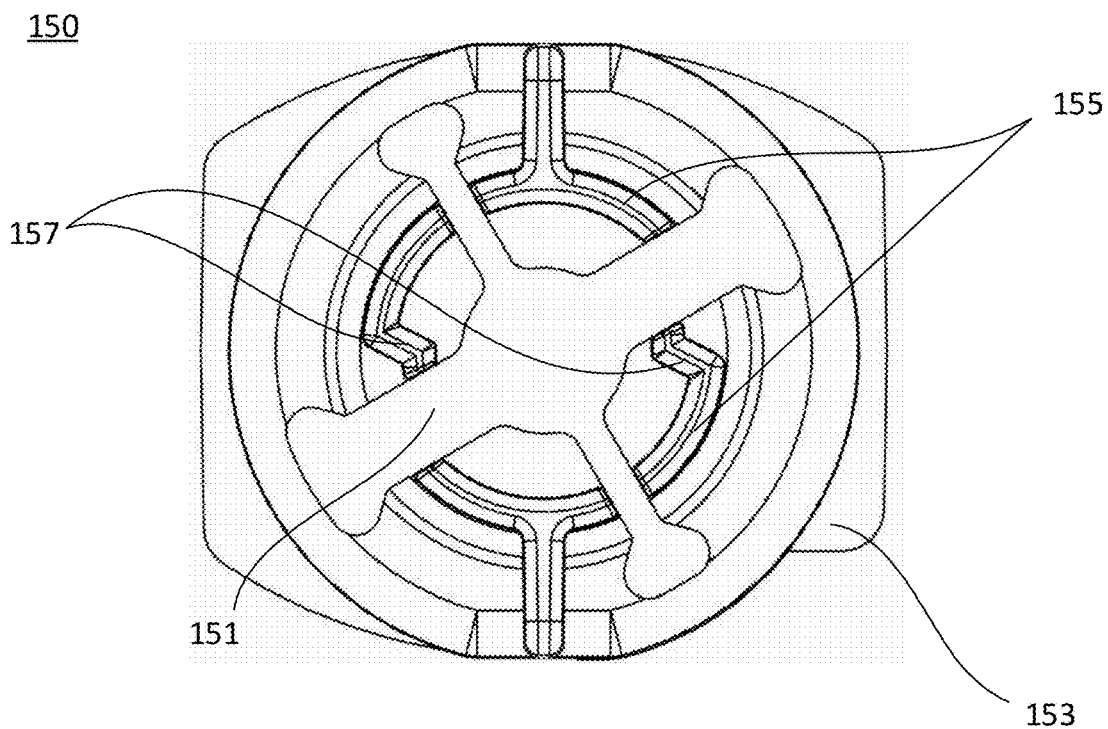
FIGS. 9A-D illustrate various views of a spring retainer component of an injector training device.
Figure 9B:
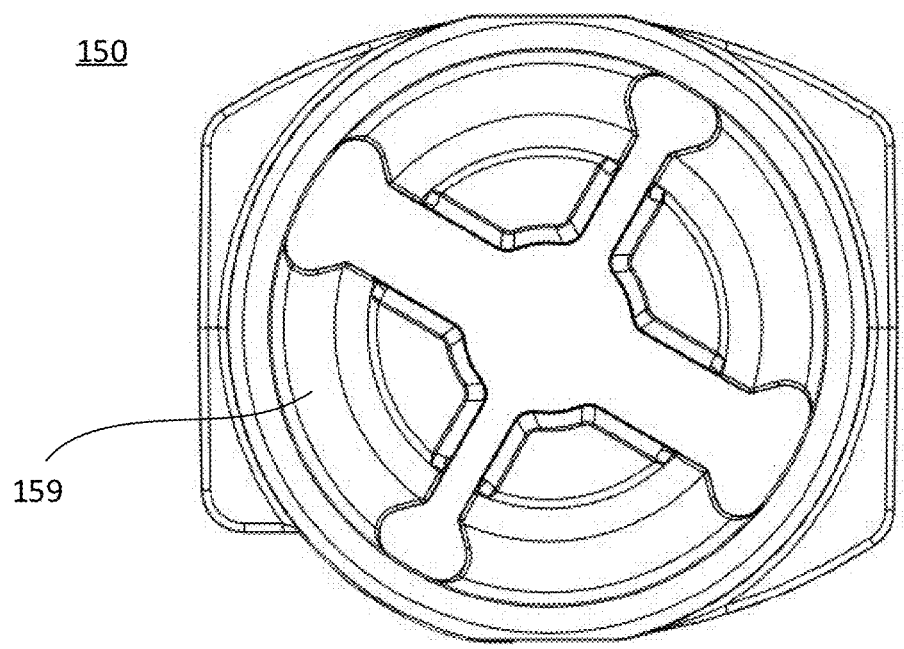
Figure 9C:
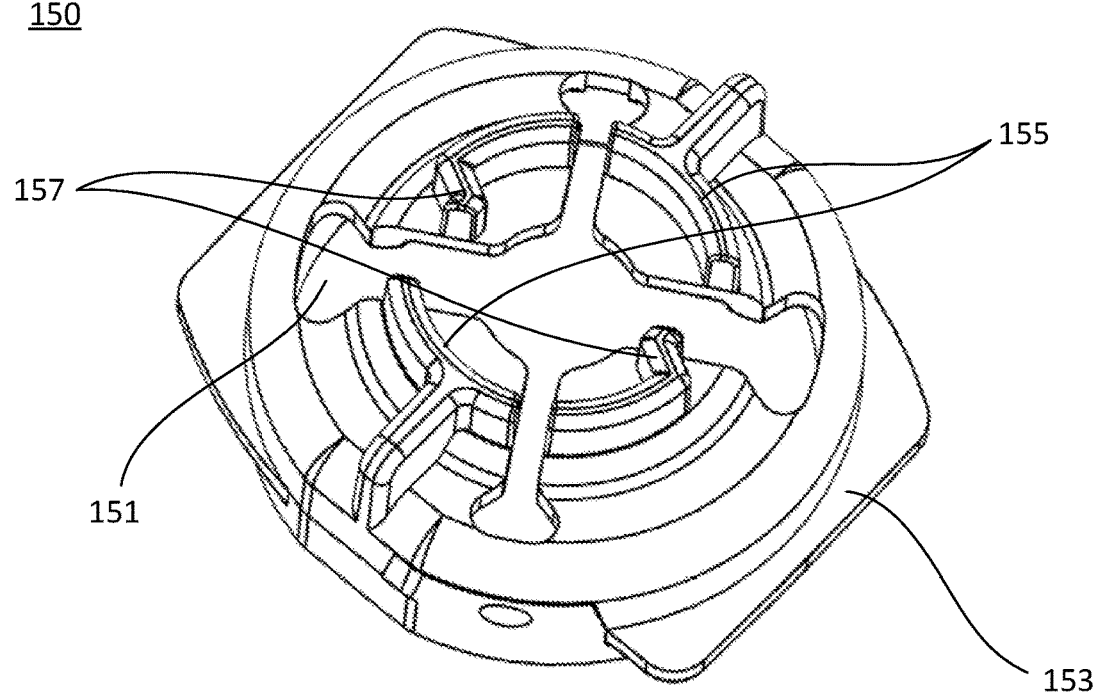
Figure 9D:
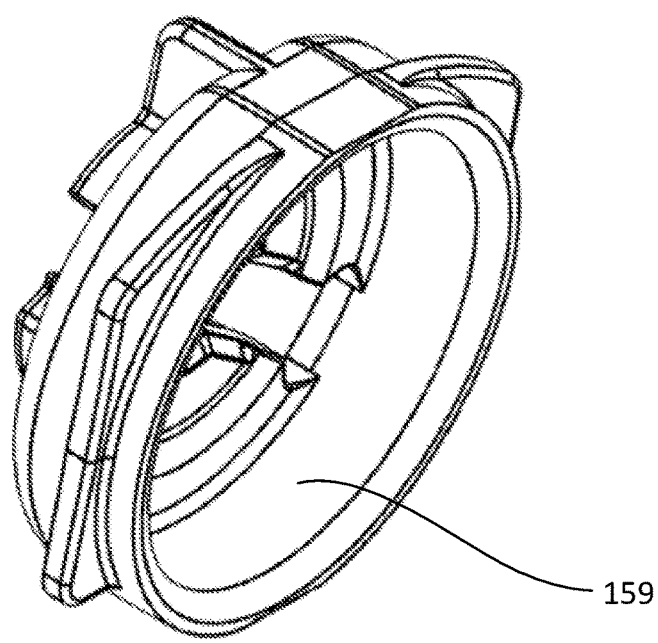

FIGS. 8A-C illustrate various views of the frame 140 of the injector training device 100, including a cross-sectional perspective view FIG. 8B. As mentioned, frame 140 includes frame protrusions 142 that interface with various features of the cap 160 that is illustrated in FIGS. 10A-D. For example, when in stowed and ready state, the frame protrusions rest within an inner recess 161 formed along an inner sidewall of the cap. Inner protrusions 162 of the cap interferingly engage frame protrusions 142 (or vice versa) when the cap 160 is rotated with respect to the housing 110. The interfering engagement as noted above is meant to mimic the pressure needed to rotate the cap in an actual injector device and/or overcome tearing a safety seal or sticker. The inner protrusion and frame protrusion also provide another clicking sound when passing by each other. The frame protrusion 142 when engaged with the cap in one position is disposed between the recess ledge/flange 163 and the inner surface of cap flange 165. Cap flange notches 166 allow the cap to be removed from frame protrusions 142 and away from the housing when the frame protrusion 142 is aligned with the notches 166. Various positions of this are further illustrated in FIGS. 12F.1-5 and removal of the cap from the housing as shown in FIG. 12H. In similar manner, the cap can be put back on again by aligning the notches with the frame protrusions and then rotating to reset it back to the stowed and ready state, such as shown in FIGS. 12AA, 12CC.1-5 and 12DD.1-2.

Figure 11A:
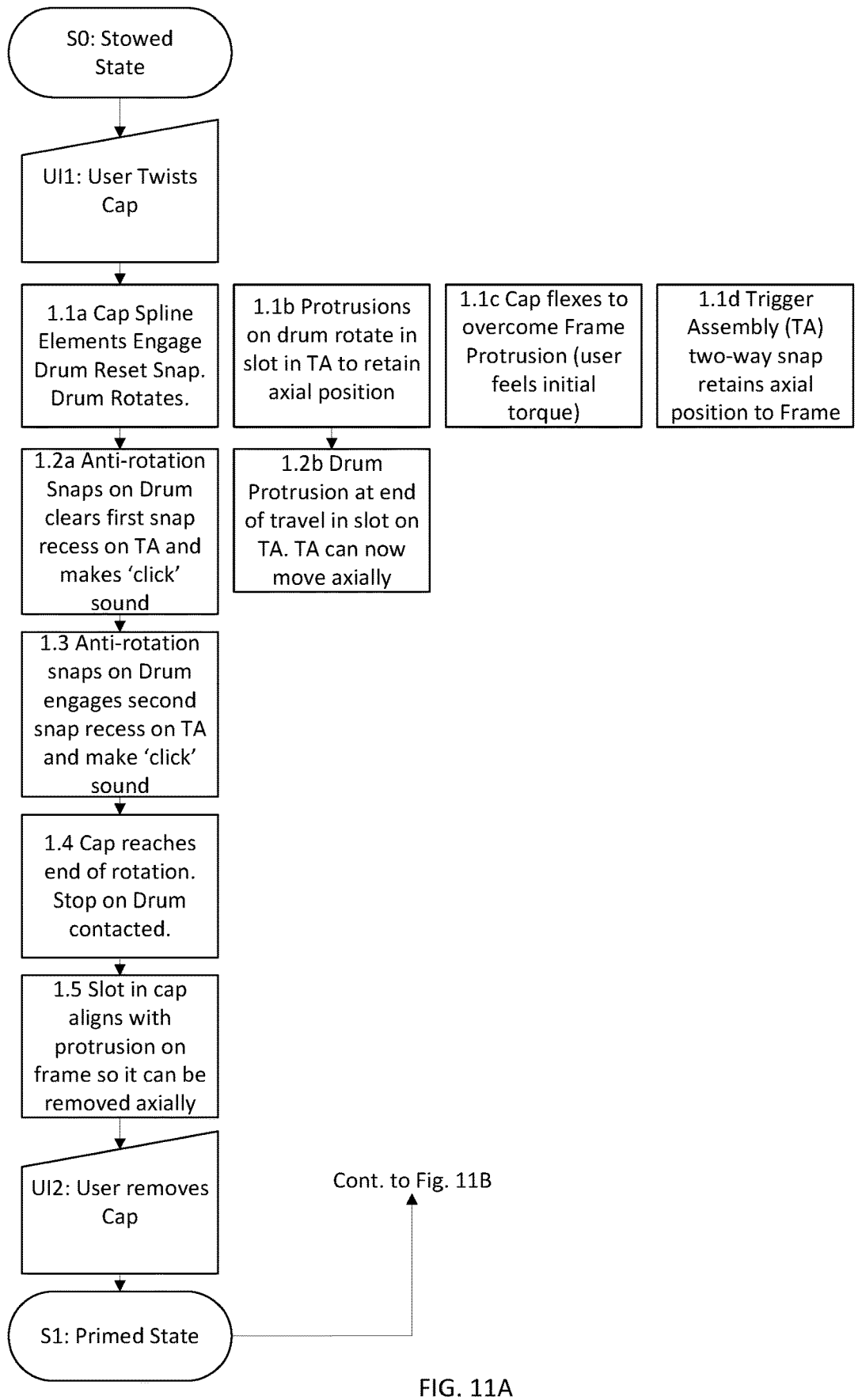
Figure 11B:
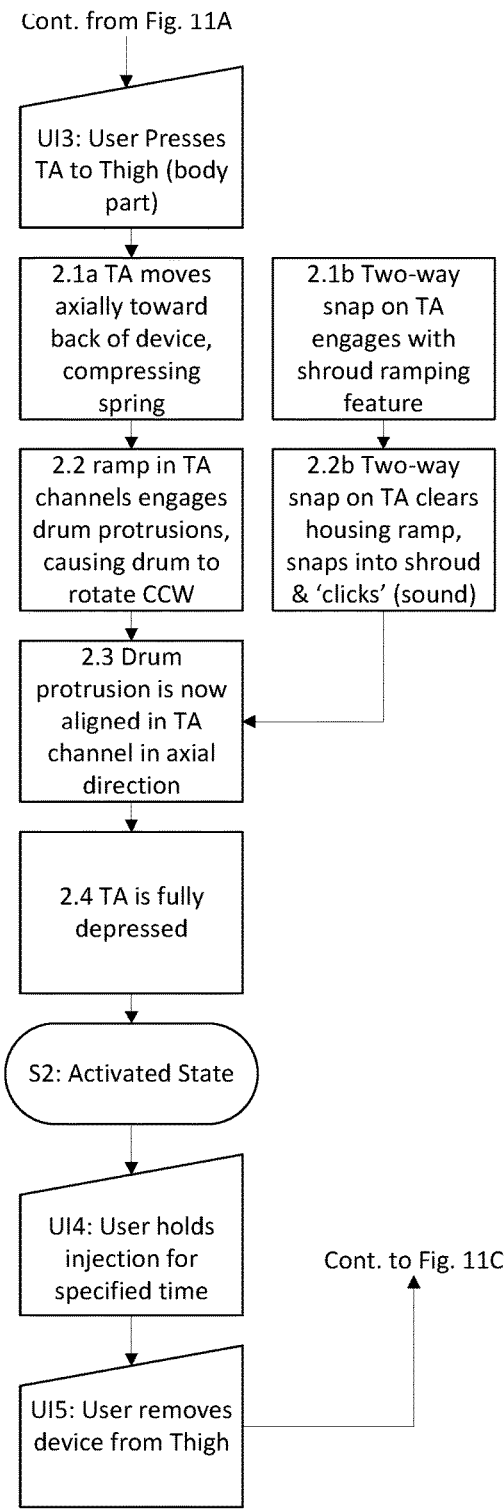
Figure 11C:
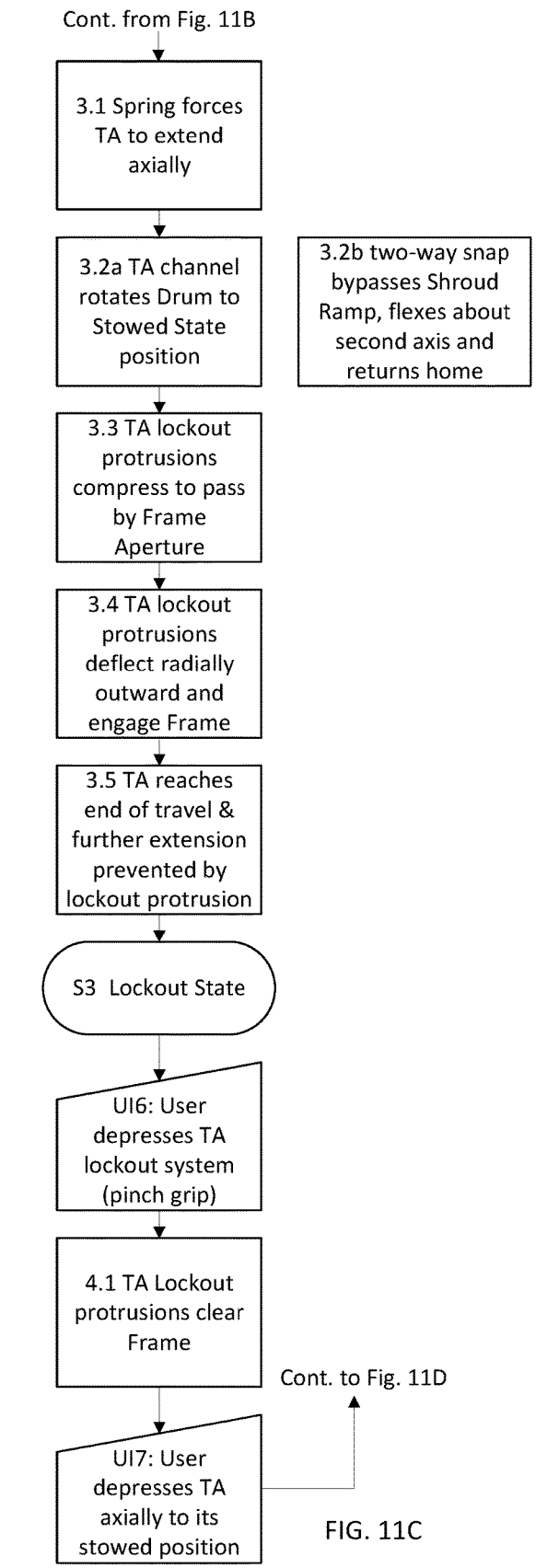

FIGS. 11A-E illustrate a diagram of steps and methods involving user interaction, processes and states associated with the injector training device 100. Each of the boxes designated with S and an oblong shape are indicative of the various states of the injector training device. For example, S0 shown in FIG. 11A is the training device in its initial stowed state. The other states include S1 a primed state indicative of the primed state of a real autoinjector mixing and delivery device, where the medicaments disposed inside have been mixed and the device is in a state to have the needle injected into a user and deliver the mixed medicament. The S2 is the activated state where the bump trigger of a real autoinjector device has been depressed, which in turn fires the needle into the user and forces the mixed medicament through the needle into the user. Here the trigger assembly 120 is equivalent to the bump trigger. S3 is a lockout state, where the needle shield, which also functions as a bump trigger in a real autoinjector device, prevents the user from re-depressing the bump trigger and injuring themselves on the exposed needle. For the trainer device, again that trigger assembly is meant to mimic the needle shield and as noted above lockout protrusions 122 prevent the trigger assembly from being re-depressed (as if a needle was exposed).

The trapezoidal boxes with the UI designation are indicative of the user interaction steps with the training device, that mimic similar steps with a real autoinjector device. The UI1 step is where the user twists or rotates the cap with respect to the housing. Each of the square or rectangular boxes are indicative of the internal features of the training and how those features are interacting with each other given the user interaction with the training device. They are designated with the same numerical number as that of the UI boxes indicating what is occurring during that user interaction. For this first step these include the cap spline interacting with the drum reset snap, causing the drum assembly to rotate and through the rotations a first and second click are heard, various features are able to move in a particular manner as noted above.

During the second user interaction UI2 the user is able to remove the cap, this then allows the trigger assembly to be exposed places the trainer device in a primed state to be activated.

During the third user interaction UI3 the user presses the exposed portion of the trigger assembly against a part of the user's body, such as a thigh. This depressing of the trigger assembly actuates the training device causing the compressed spring to extend the trigger assembly further out of the housing. Clicking noises are heard similar to those when the real autoinjector device is actuated.

This places the training device (which mimics the real device) in an activated state. The fourth user interaction is to hold the training device against the body portion, such as the thigh, for a specified time. This interaction mimics allowing the medicine to completely flow from the autoinjector device into the portion of the body where the medicament was injected therein. This step is often a critical or important step, depending on the medicament, as delivering and allowing the device to deliver the appropriate amount of medicament can be critical to the care of the patient.

After the user waits the specified time, the fifth user interaction step is to remove the device from the mimicked injection spot. Once removed the training device now fully extends the trigger assembly and the lockout protrusions prevent re-depressing. This now places the training device in the lockout state, which is the state where the user of a real injector device would then dispose of the used device.

However, for the present training device 100, and as noted above it is configured to be resettable to go through the above steps again, multiple times, thus being able to adequately train would be users.

The sixth user interaction step UI6 involves the user pinching the system 121 to clear the lockout protrusions, so the trigger assembly can be re-depressed and reset within the housing. As the pinching and flexing inward of system 121 occurs the user during the seventh interaction step UI7, axially depresses the trigger assembly into the housing. As noted in the diagram this causes the spring to be compressed and the two-way snap 125 to make a clicking sound indicative that the trigger assembly has been reset.

The eighth user interactive step has the user replacing the cap back onto the frame by aligning the notches with the frame protrusions as noted above. This process aligns the cap gear/spline with the reset snaps. The user pushes the cap in until the cap flange abuts against the frame flange. In some embodiments the frame flange and the housing are aligned in the same plane, so the cap flange would abut against both the end of the housing and the frame flange 146.

The ninth user interactive step has the user rotate the cap clockwise until it is in its stowed state and ready for another use. Through this rotation spline passes by the reset snap and the frame protrusion passes by the inner protrusion of the cap where each make a clicking sound. These sounds can be simultaneous or they can be sequential until everything is fully aligned. Now the training is ready for another use.

FIGS. 12A-GG provide illustrations of each of the various steps of the diagram of FIGS. 11A-E and the interactions that are occurring during each of the user interactive steps.

Of course, the present invention is not limited to the above features and advantages. Those of ordinary skill in the art will recognize additional features and advantages upon reading the following detailed description, and upon viewing the accompanying drawings.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

What is claimed is:

1. An injector training device comprising:
   a housing (110);
   a trigger assembly (120) at least partially disposed within the housing;
   a drum assembly (130) at least partially disposed within the trigger assembly, wherein the drum assembly has at least one drum protrusion (131) configured to engage a drum protrusion channel (123) formed in a sidewall of the trigger assembly; and
   a frame (140) disposed over the trigger assembly (120);
   wherein the frame includes at least one frame protrusion (142) that is configured to interface with an inner protrusion of a cap, and wherein the interface between the inner protrusion and the frame protrusion creates an interference force when rotating the cap with respect to the housing.

2. The injector training device of claim 1, wherein the drum assembly further includes anti-rotation snaps (134) configured to correspond to at least one recess (126) formed in the sidewall of the trigger assembly, and wherein the anti-rotation snaps (134) are configured to allow the drum to rotate in one direction.

3. The injector training device of claim 2, wherein the anti-rotation snaps (134) cause a clicking sound when the drum assembly is rotated a first distance with respect to the trigger assembly.

4. The injector training device of claim 3, wherein the anti-rotation snaps cause a second clicking sound when the drum assembly is rotated a second distance with respect to the trigger assembly.

5. The injector training device of claim 1, wherein the drum assembly further includes at least one drum reset snap (136) that is configured to interface with a portion of a cap 160.

6. The injector training device of claim 1, wherein the cap further includes a spline (164) disposed in a cavity portion (168) of the cap.

7. The injector training device of claim 1, wherein the cap further includes a flange (165) configured to interface with the frame protrusion.

8. The injector training device of claim 1, further including a spring retainer (150) configured to hold a spring (152) in place between the spring retainer and the trigger assembly (120).

9. The injector training device of claim 8, wherein actuating the trigger assembly causes the spring to extend the trigger assembly in an activated state.

10. The injector training device of claim 1, wherein the trigger assembly further includes a lockout snap system (121).

11. The injector training device of claim 1, wherein the trigger assembly further includes a two-way snap element (125) that interfaces with a ramp feature of the housing.

12. The injector training device of claim 1, wherein the drum protrusion (131) is configured to engage the drum protrusion channel (123) formed in the sidewall of the trigger assembly under rotational movement of the drum protrusion (131) and axial movement of the drum protrusion (131).

13. An injector training device comprising:
    a housing (110);
    a cap (160) having an inner protrusion (162) disposed on an interior sidewall of the cap;
    a trigger assembly (120) at least partially disposed within the housing;
    a drum assembly (130) at least partially disposed within the trigger assembly, wherein the drum assembly has at least one drum protrusion (131) configured to engage a drum protrusion channel (123) formed in a sidewall of the trigger assembly, and
    wherein the drum protrusion channel forms part of a drum protrusion pathway (124); and
    a frame (140) disposed over the trigger assembly (120);
    wherein the frame includes at least one frame protrusion (142) that is configured to interface with the inner protrusion of the cap, and wherein the interface between the inner protrusion and the frame protrusion creates an interference force when rotating the cap with respect to the housing.

14. The injector training device of claim 13, wherein the trigger assembly (120) that is at least partially disposed within the housing becomes accessible upon removal of the cap.

15. The injector training device of claim 13, wherein the cap further includes a spline (164) that interfaces with a reset snap element (136) of the drum assembly.

16. The injector training device of claim 13, wherein the trigger assembly further includes a two-way snap element (125) that is configured to interface with a ramp feature (119) disposed on an inner surface of the housing (110).

17. The injector training device of claim 13, whereupon a complete cycle of the drum protrusion through the drum protrusion pathway causes the training device cycle from a stowed state, to a primed state, to an activated state, to a lockout state, and back to the stowed state.

18. An injector training device comprising:
    a housing (110);
    a cap (160) having an inner protrusion (162) disposed on an interior sidewall of the cap; and
    a frame (140) disposed at least partially in the housing wherein the frame has at least one protrusion (142) on an outer sidewall of the frame,
    wherein the at least one protrusion (142) of the frame is configured to interface with the inner protrusion (162) of the cap (160), and
    wherein the inner recess and the at least one protrusion provide a resistance to rotation of the cap with respect to the housing that mimics a resistance force required to rotate a cap about an injector device, and
    a trigger assembly (120) at least partially disposed within the housing; and
    a drum assembly (130) at least partially disposed within the trigger assembly, wherein the drum assembly has at least one drum protrusion (131) configured to engage a drum protrusion channel (123) formed in a sidewall of the trigger assembly.

* * * * *